(12) United States Patent
Chawke et al.

(10) Patent No.: US 9,789,484 B2
(45) Date of Patent: Oct. 17, 2017

(54) SYSTEM AND METHOD FOR CHARGING FLUIDS

(71) Applicant: STOKES BIO LIMITED, Carlsbad, CA (US)

(72) Inventors: Brian Chawke, Limerick (IE); Kieran Curran, Limerick (IE); David McGuire, Limerick (IE); Michael Sayers, Kerry (IE); Noel Sirr, Limerick (IE)

(73) Assignee: Stokes Bio Limited, Limerick (IE)

( * ) Notice: Subject to any disclaimer, the term of this patent is extended or adjusted under 35 U.S.C. 154(b) by 0 days.

(21) Appl. No.: 15/048,812

(22) Filed: Feb. 19, 2016

(65) Prior Publication Data

US 2016/0271606 A1 Sep. 22, 2016

Related U.S. Application Data

(63) Continuation of application No. 14/110,678, filed as application No. PCT/US2012/032590 on Apr. 6, 2012, now abandoned.

(60) Provisional application No. 61/473,317, filed on Apr. 8, 2011.

(51) Int. Cl.

| B05B 5/053 | (2006.01) |
|---|---|
| B01L 3/00 | (2006.01) |
| B01F 13/00 | (2006.01) |
| G01N 1/38 | (2006.01) |
| B01J 19/08 | (2006.01) |
| B05B 5/035 | (2006.01) |
| C12Q 1/68 | (2006.01) |
| G01N 1/40 | (2006.01) |

(52) U.S. Cl.
CPC ...... *B01L 3/50273* (2013.01); *B01F 13/0071* (2013.01); *B01F 13/0076* (2013.01); *B01J 19/087* (2013.01); *B01L 3/502715* (2013.01); *B01L 3/502784* (2013.01); *B01L 3/52* (2013.01); *B01L 3/56* (2013.01); *B05B 5/035* (2013.01); *C12Q 1/686* (2013.01); *G01N 1/38* (2013.01); *B01L 2200/0673* (2013.01); *B01L 2300/0867* (2013.01); *B01L 2400/0406* (2013.01); *B01L 2400/0415* (2013.01); *G01N 2001/4038* (2013.01)

(58) Field of Classification Search
CPC .......... B32B 37/0046; B01L 3/56; B01L 3/00
USPC ................................ 361/212, 220, 225, 222
See application file for complete search history.

(56) References Cited

U.S. PATENT DOCUMENTS

| 2,357,355 A | 9/1944 | Penney | |
|---|---|---|---|
| 2,672,948 A | 3/1954 | Penney | |
| 3,300,661 A * | 1/1967 | Talaat | H01J 45/00 310/306 |

(Continued)

OTHER PUBLICATIONS

PCT/US2012/032590 International Search Report with Written Opinion dated Sep. 14, 2012.

*Primary Examiner* — Thienvu Tran
*Assistant Examiner* — Lucy Thomas

(57) ABSTRACT

Devices, systems, and methods for charging fluids are disclosed. The charging of fluids improves the mixing of fluids in microfluidic systems. The charging is performed by producing an ion field between an ionizing electrode and an opposed ground electrode. A fluid-containing vessel is positioned between the opposed electrodes and the ion field charges the fluid in the vessel.

25 Claims, 26 Drawing Sheets

(56) References Cited

U.S. PATENT DOCUMENTS

| | | | | |
|---|---|---|---|---|
| 3,479,549 A * | 11/1969 | Baker | .................... | H01J 17/04 |
| | | | | 313/297 |
| 4,291,226 A * | 9/1981 | Rueggeberg | ............ | H01T 19/00 |
| | | | | 204/164 |
| 5,012,094 A | 4/1991 | Hamade | | |
| 5,077,468 A | 12/1991 | Hamade | | |
| 5,756,047 A * | 5/1998 | West | ......................... | A61L 2/18 |
| | | | | 422/124 |
| 6,330,834 B1 * | 12/2001 | Weitzman | ............ | G01N 1/2035 |
| | | | | 73/863.71 |
| 6,624,377 B2 * | 9/2003 | Gianchandani | .......... | B23H 1/00 |
| | | | | 219/69.13 |
| 6,717,792 B2 * | 4/2004 | Gorczyca | ................ | H01T 23/00 |
| | | | | 361/212 |
| 2007/0009411 A1 * | 1/2007 | Ray | ................... | B01D 46/0035 |
| | | | | 423/210 |
| 2010/0294048 A1 * | 11/2010 | McGuire | .............. | B01L 3/0293 |
| | | | | 73/864.34 |

* cited by examiner

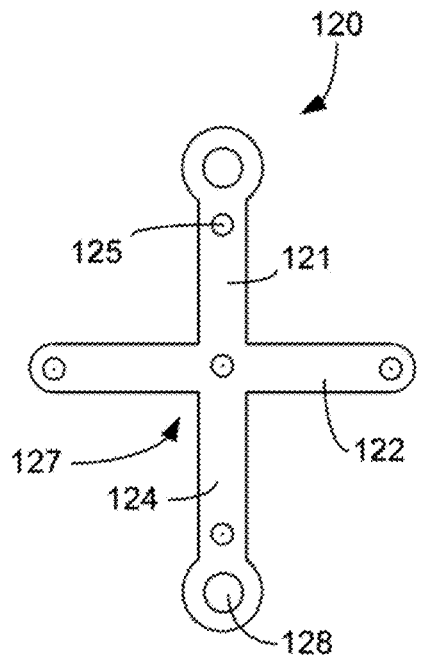
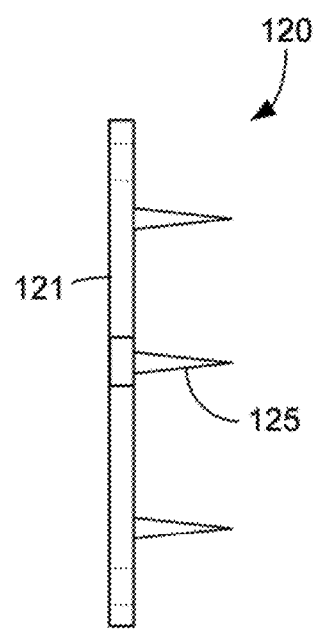
FIG. 3a                FIG. 3b
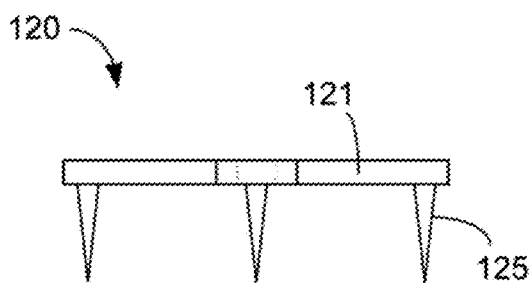
FIG. 3c

SYSTEM AND METHOD FOR CHARGING FLUIDS

CROSS-REFERENCE TO RELATED APPLICATIONS

This application is a continuation of U.S. application Ser. No. 14/110,678, filed Dec. 18, 2013, which is a 371 of International Application No. PCT/US2012/032590, filed Apr. 6, 2012, which claims the benefit of U.S. Provisional Application No. 61/473,317, filed Apr. 8, 2011, all of which are incorporated herein by reference.

TECHNICAL FIELD

This disclosure is directed to systems and methods for charging fluids to improve the admixture of fluids, such as, for example, in microfluidic systems.

BACKGROUND

Microfluidics involves micro-scale systems and devices that handle small volumes of fluids. Because microfluidics can accurately and reproducibly control and dispense small fluid volumes, in particular volumes less than 1 µL, application of microfluidics has the capability to provide significant cost-savings in technical fields such as, for example, chemical, biochemical, and biological sample processing. The use of microfluidics technology can reduce cycle times, shorten time-to-results, and increase throughput in various applications. Furthermore, incorporation of microfluidics technology can enhance system integration and automation in various applications.

Given the relatively small dimensions of microfluidic devices or components thereof, microfluidic systems involve construction and design that differs from macro-scale fluidic systems. Simple scaling down in size of macro-scale devices to a microfluidic scale is often not a successful design option. For example, liquid flow in microfluidic devices physically differs from that of macro-scale size devices. Because liquid flow tends to be laminar, surface flux and surface tension start to dominate and, as a result, physical effects not seen at the macro-scale become significant at the microfluidic scale. Other differences at the microfluidic scale include, for example, faster thermal diffusion, predominately laminar flow, significant capillary forces, and significant electrostatic forces.

SUMMARY

Embodiments disclosed herein are directed to a fluid charging system configured to charge a fluid contained in a fluid vessel. The fluid charging system comprises an ionizing electrode and a ground electrode. The ionizing electrode and the ground electrode are positioned adjacent to the fluid vessel. The ionizing electrode and the ground electrode are opposed so that the fluid vessel is positioned between the ionizing electrode and the ground electrode. The ionizing electrode and the ground electrode are configured to produce an ion field that contacts fluid contained in the fluid vessel, thereby charging the fluid.

Other embodiments disclosed herein are directed to a method for charging a fluid contained in a vessel. The method comprises producing an ion field between an ionizing electrode and a ground electrode. A fluid-containing vessel is positioned adjacent to and between the ionizing electrode and the ground electrode so that the fluid vessel is positioned between the ionizing electrode and the ground electrode. The ion field produced by the ionizing electrode and the ground electrode contacts fluid contained in the fluid vessel, thereby charging the fluid.

It is understood that the invention disclosed and described in this specification is not limited to the embodiments disclosed in this Summary.

BRIEF DESCRIPTION OF THE DRAWINGS

Various features and characteristics of the non-limiting and non-exhaustive embodiments disclosed and described in this specification may be better understood by reference to the accompanying figures, in which:

FIG. 3a is a bottom view of a cross-shaped ionizing electrode comprising a cross-shaped emitter plate and five emitter pins; FIGS. 3b and 3c are side views of the ionizing electrode shown in FIG. 3a.

FIGS. 5b and 5c are side views of the ionizing electrode shown in FIG. 5a.

FIG. 6b is a side view of the assembly shown in FIG. 6a.

FIG. 7b is a side view of the assembly shown in FIG. 7a.

FIG. 21b is a side view of the ground electrode shown in FIG. 21a.

Figure 1:
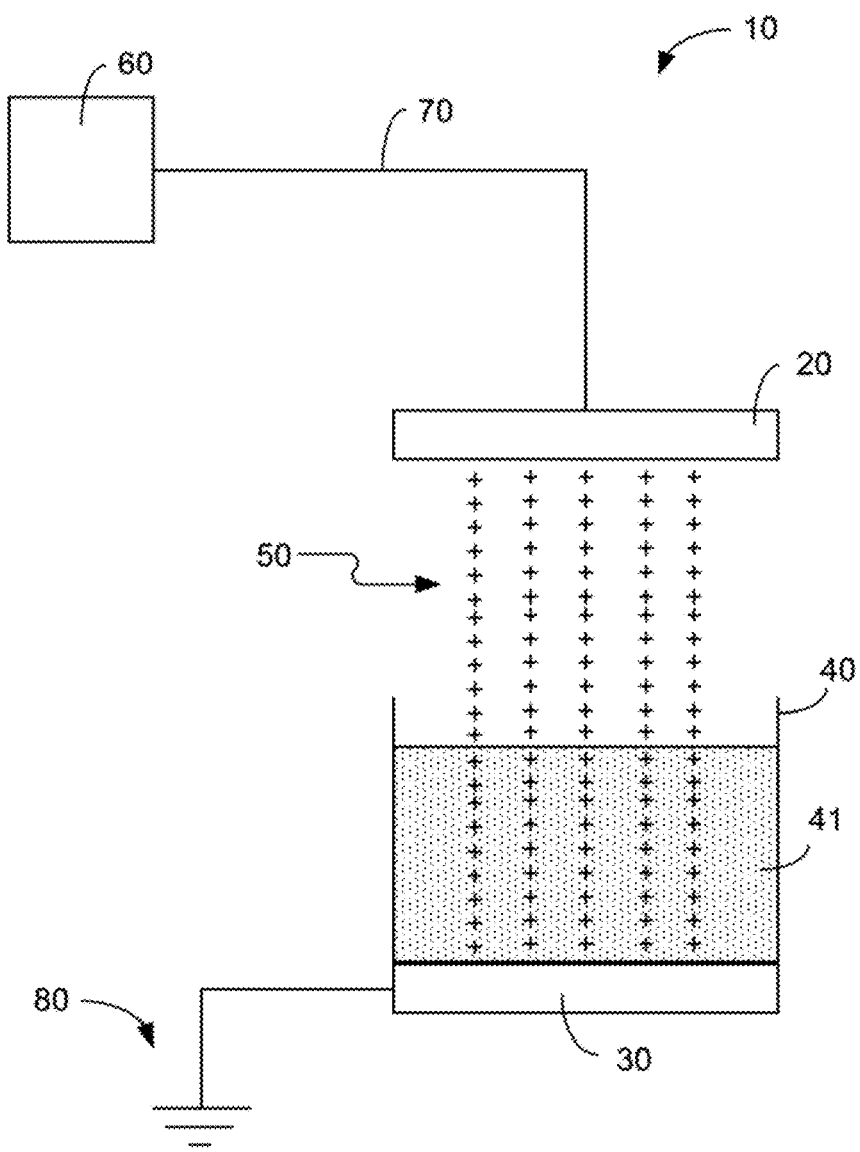
FIG. 1 is a side view schematic diagram illustrating a fluid charging system comprising an ionizing electrode and a ground electrode that produce an ion field.

The reader will appreciate the foregoing details, as well as others, upon considering the following detailed description of various non-limiting and non-exhaustive embodiments according to the present disclosure.

DETAILED DESCRIPTION

Various embodiments are described and illustrated in this specification to provide an overall understanding of the structure, function, operation, manufacture, and use of the disclosed devices, systems, and methods. It is understood that the various embodiments described and illustrated herein are non-limiting and non-exhaustive. Thus, the invention is not limited by the description of the various non-limiting and non-exhaustive embodiments disclosed in this specification. Rather, the invention is defined solely by the claims. The features and characteristics illustrated and/or described in connection with various embodiments may be combined with the features and characteristics of other embodiments. Such modifications and variations are intended to be included within the scope of this specification. As such, the claims may be amended to recite any features or characteristics expressly or inherently described in, or otherwise expressly or inherently supported by, this specification. Further, Applicants reserve the right to amend the claims to affirmatively disclaim features or characteristics that may be present in the prior art. Therefore, any such amendments would comply with the requirements of 35 U.S.C. §112, first paragraph, and 35 U.S.C. §132(a). The various embodiments disclosed and described herein can comprise, consist of, or consist essentially of the features and characteristics as variously described herein.

Any patent, publication, or other disclosure material that is said to be incorporated by reference herein, is incorporated herein in its entirety unless otherwise indicated, but only to the extent that the incorporated material does not conflict with existing definitions, statements, or other disclosure material expressly set forth in this disclosure. As such, and to the extent necessary, the express disclosure as set forth herein supersedes any conflicting material incorporated by reference herein. Any material, or portion thereof, that is said to be incorporated by reference herein, but which conflicts with existing definitions, statements, or other disclosure material set forth herein is only incorporated to the extent that no conflict arises between that incorporated material and the existing disclosure material. Applicant reserves the right to amend the present disclosure to expressly recite any subject matter, or portion thereof, incorporated by reference herein.

Reference throughout this specification to "various embodiments," or the like, means that a particular feature or characteristic described in connection with the embodiment is included in at least one embodiment. Thus, use of the phrase "in various embodiments," or the like, in this specification does not necessarily refer to a common embodiment, and may refer to different embodiments. Further, the particular features or characteristics may be combined in any suitable manner in one or more embodiments. Thus, the particular features or characteristics illustrated or described in connection with various embodiments may be combined, in whole or in part, with the features or characteristics of one or more other embodiments without limitation. Such modifications and variations are intended to be included within the scope of the present disclosure. In this manner, the various embodiments described in this specification are non-limiting and non-exhaustive.

In various embodiments, a fluid charging system configured to charge a fluid contained in a fluid vessel comprises an ionizing electrode and a ground electrode. The ionizing electrode and the ground electrode may be positioned adjacent to the fluid vessel. The ionizing electrode and the ground electrode may be opposed so that the fluid vessel is positioned between the ionizing electrode and the ground electrode. The ionizing electrode and the ground electrode are configured to produce an ion field that contacts fluid contained in the fluid vessel, thereby charging the fluid.

In various embodiments, a method for charging a fluid contained in a vessel comprises producing an ion field between an ionizing electrode and a ground electrode. A fluid-containing vessel may be positioned adjacent to and between the ionizing electrode and the ground electrode. The ion field produced by the ionizing electrode and the ground electrode contacts the fluid contained in the fluid vessel, thereby charging the fluid. The devices, systems, and methods disclosed herein may be used to produce a net charge in various fluids.

Fluid charged in the devices, systems, and methods disclosed herein may be mixed with other fluids after being charged. The net charge carried by the fluids charged in the devices, systems, and methods disclosed herein may increase the extent of the mixing of fluids in downstream devices, systems, and methods. For instance, fluids carrying a net charge may exhibit improved mixing with other miscible fluids when mixed with fluid plugs or droplets in an immiscible carrier fluid in microfluidic system. In this manner, the net charge may decrease undesirable static electric effects observed in microfluidic systems that can adversely affect fluid mixing.

FIG. 1 illustrates a fluid charging system 10 according to various embodiments. The fluid charging system 10 comprises an ionizing electrode 20 positioned adjacent to a fluid vessel 40 and a ground electrode 30 positioned adjacent to the fluid vessel 40. The ionizing electrode 20 is connected to an electrical power source 60 via an electrical line 70. The ground electrode 30 is grounded relative to the ionizing electrode 20 as indicated at 80. The ionizing electrode 20 and the ground electrode 30 produce an ion field 50 that contacts a fluid 41 contained in the fluid vessel 40, thereby charging the fluid 41. The ionizing electrode 20 and the ground electrode 30 are opposed so that the fluid vessel 41 is positioned between the ionizing electrode 20 and the ground electrode 40. The ionizing electrode 20 is positioned adjacent to an open top end of the fluid vessel 40, which facilitates contact between the ion field 50 and the fluid 41.

In various embodiments, a fluid charging system comprises one or more fluid sampling devices configured to withdraw charged fluid from the fluid vessel, such as described and illustrated below. In various embodiments, the fluid sampling devices may comprise one or more tubes, such as, for example, capillary tubes, configured to withdraw charged fluid from the fluid vessel. In various embodiments, the fluid sampling devices may comprise one or more sheaths, wherein each sheath surrounds one or more tubes, such as, for example, capillary tubes, configured to withdraw charged fluid from the fluid vessel. In various embodiments, the one or more fluid sampling devices may be in continuous or discontinuous fluid communication with the fluid vessel.

In various embodiments, fluid sampling devices may be configured to withdraw segmented plugs or droplets of charged fluid from a fluid vessel. The withdrawal and acquisition of charged fluid may be performed in either a continuous operation or batch operation mode. For example, fluid sampling devices may comprise, for example, the devices described in United States Patent Application Publication Nos. 2010/0304443 and 2010/0294048, which are incorporated by reference herein. The devices described in United States Patent Application Publication Nos. 2010/0304443 and 2010/0294048 may be configured to withdraw segmented fluid samples from a vessel, wherein the segmented fluid samples are surrounded by an immiscible carrier fluid.

Fluid charging systems including fluid sampling devices may further include at least one robotics system to control the fluid sampling devices. The robotics systems may control movement of the sampling devices to control sample acquisition from the fluid vessel. In various embodiments, the driving force for the withdrawal of charged fluid by a fluid sampling device may be provided by one or more pumps. An exemplary pump is shown in International Patent Application Publication No. WO 2007/091229, which is incorporated by reference herein. In various embodiments, the fluid sampling devices may be configured to withdraw fluid using the hydrostatic siphoning effect described in United States Patent Application Publication No. 2010/0120635, which is incorporated by reference herein.

Figure 2:
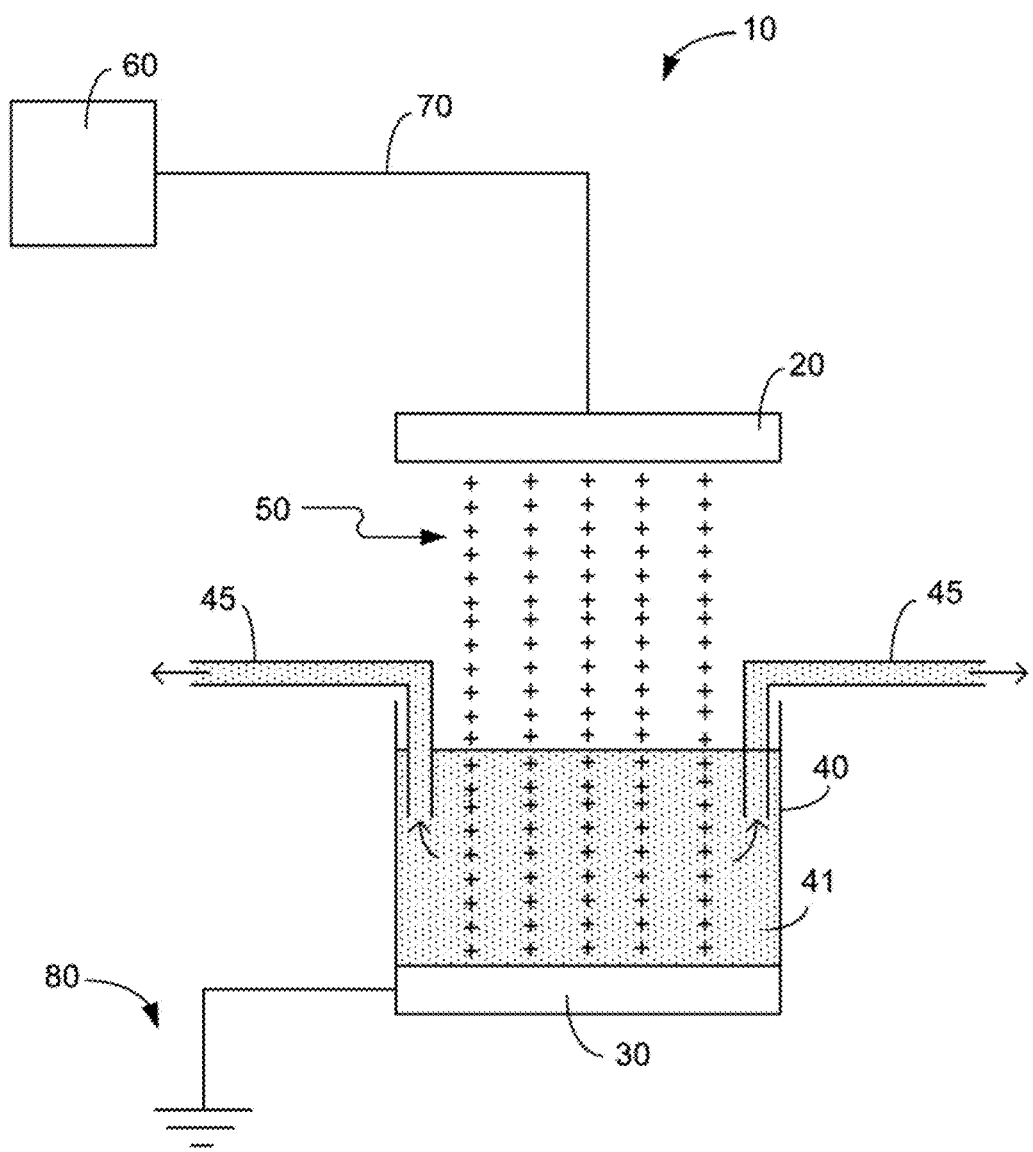
FIG. 2 is a side view schematic diagram illustrating a fluid charging system comprising an ionizing electrode, a ground electrode, a fluid vessel, and fluid sampling devices in fluid communication with the fluid vessel.
Figure 3D:
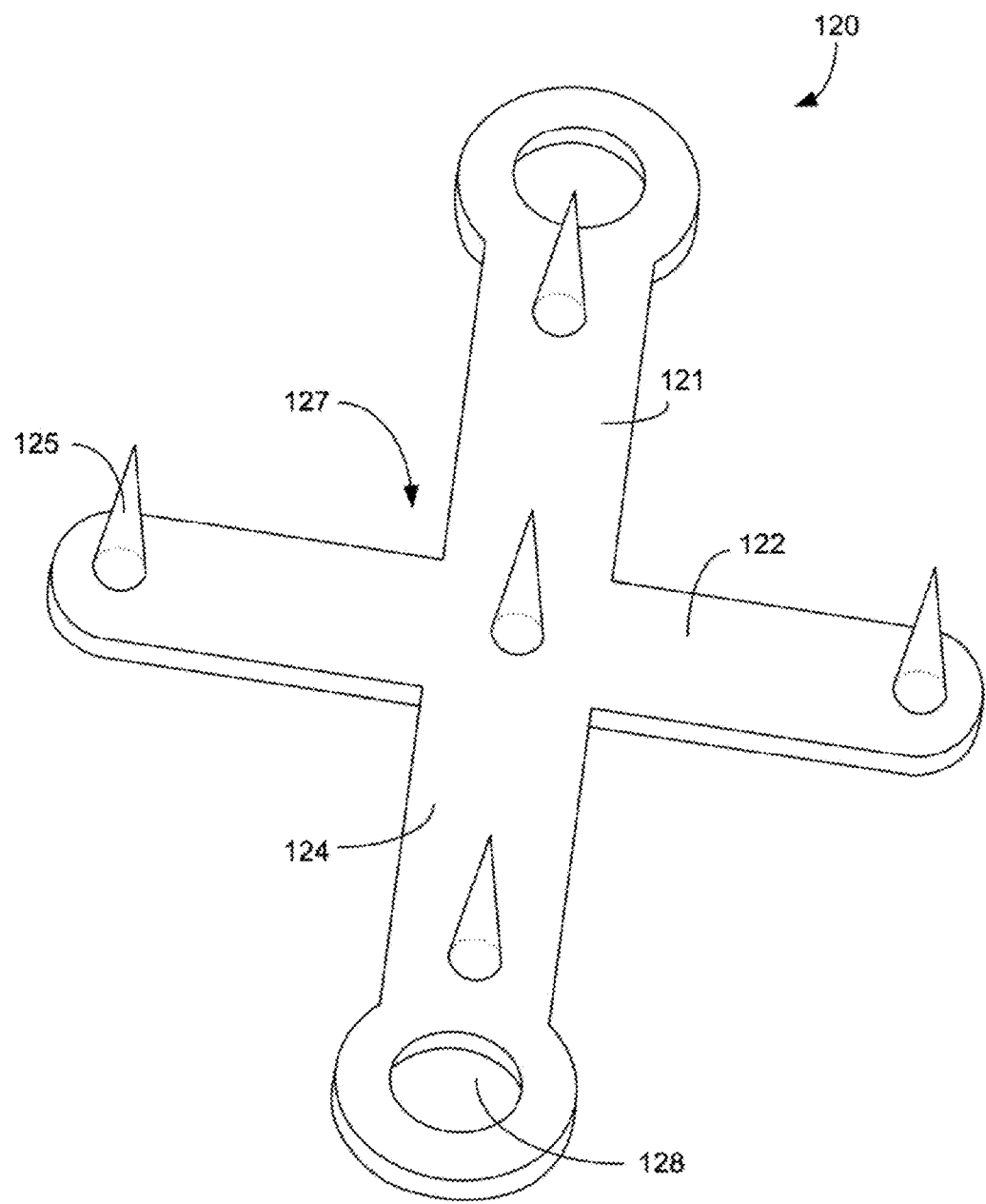
FIG. 3d is a perspective bottom view of the ionizing electrode shown in FIGS. 3a, 3b, and 3c.

FIG. 2 illustrates a fluid charging system 10 comprising fluid sampling devices 45 in fluid communication with a fluid vessel 40. The fluid sampling devices 45 are configured to withdraw a fluid 41 from the fluid vessel 40, wherein the withdrawn fluid 41 has been charged by the ion field 50. Although FIG. 2 illustrates a fluid charging system 10 comprising two (2) fluid sampling devices 45, it is understood that in various embodiments of the fluid charging systems disclosed herein, one (1) fluid sampling device may be employed or any plurality of fluid sampling devices may be employed.

In various embodiments, the ionizing electrode comprises an emitter plate and one or more emitter pins connected to the emitter plate. The emitter plate may be made of a conductive metallic material, such as, for example, a stainless steel alloy. The emitter pins may be made of a metallic or ceramic material comprising tungsten. For instance, the emitter pins may comprise tungsten carbide, such as, for example, emitter pins made of tungsten carbide or a cemented tungsten carbide (cermet) composite material. Alternatively, the emitter pins may be made of a metal alloy comprising tungsten, for example.

The emitter pins may be connected to a common side of the emitter plate by soldering, for example. The emitter pins may be connected to a common side of the emitter plate by other joining techniques, such as, for example brazing, welding, and threaded connection. For instance, the emitter pins may comprise a male threaded stub and the emitter plate may comprise corresponding female threaded bores or through-holes. Threaded mechanical connection of the emitter pins to the emitter plate may allow for the emitter pins of the ionizing electrode to be replaced without having to also replace the emitter plate.

Figure 4:
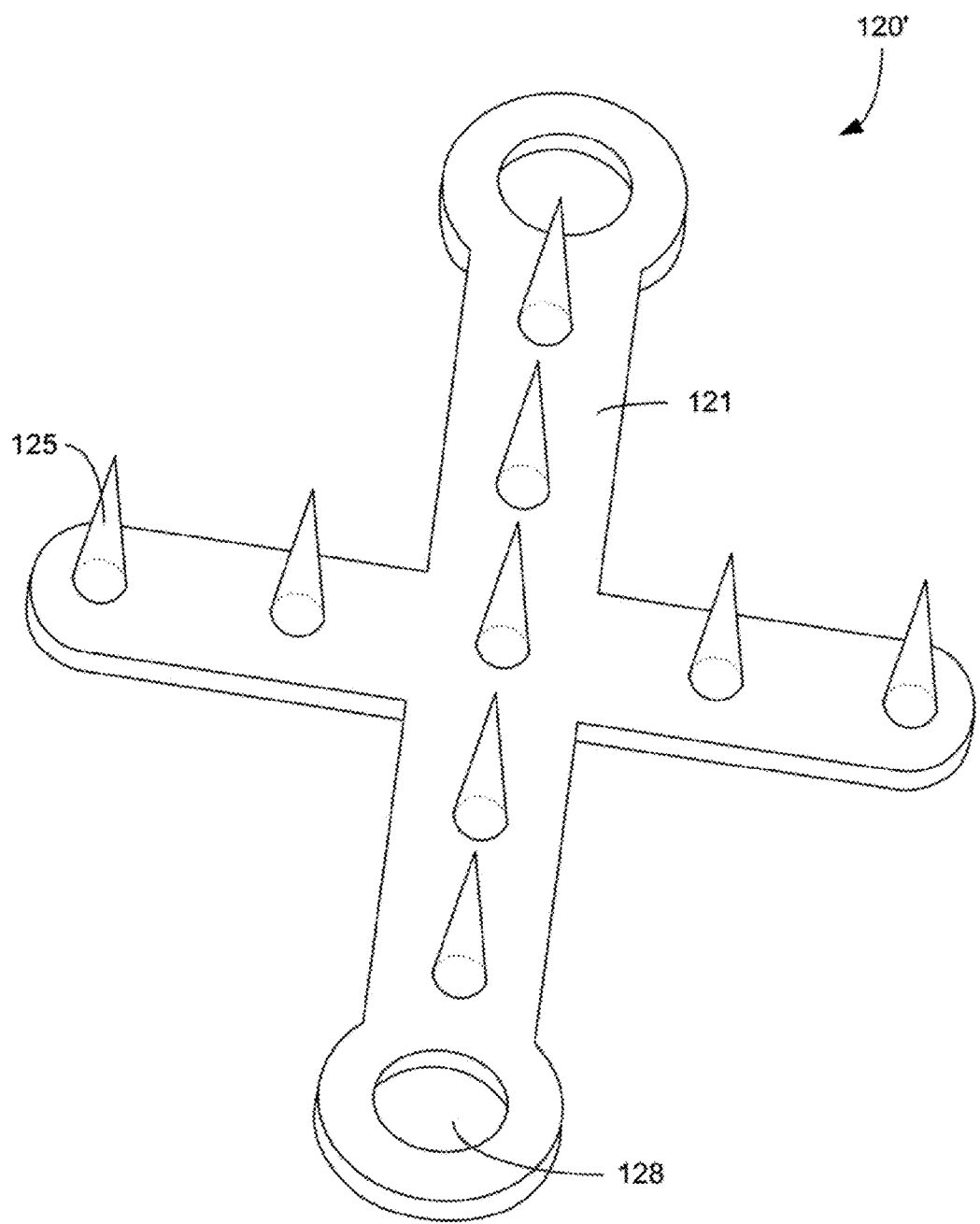
FIG. 4 is a perspective bottom view of an ionizing electrode comprising a cross-shaped emitter plate and nine emitter pins.
Figure 5A:
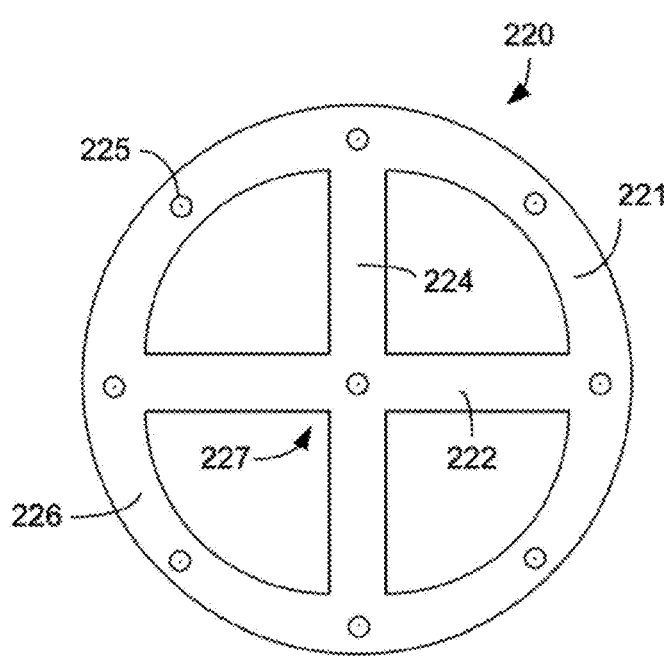
FIG. 5a is a bottom view of an annular- and cross-shaped ionizing electrode comprising an annular- and cross-shaped emitter plate and nine emitter pins.
Figure 5B:
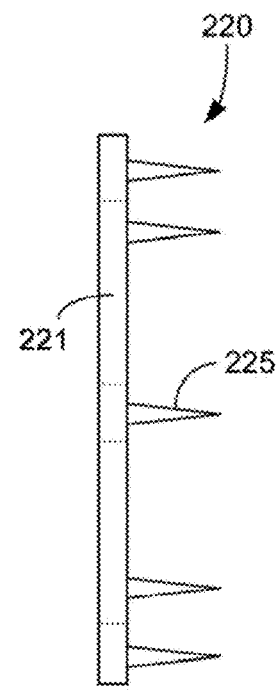
Figure 5C:
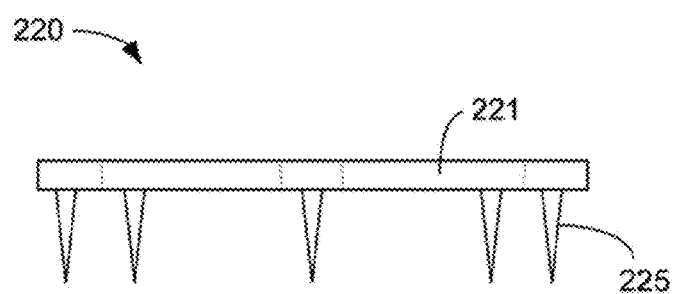
Figure 5D:
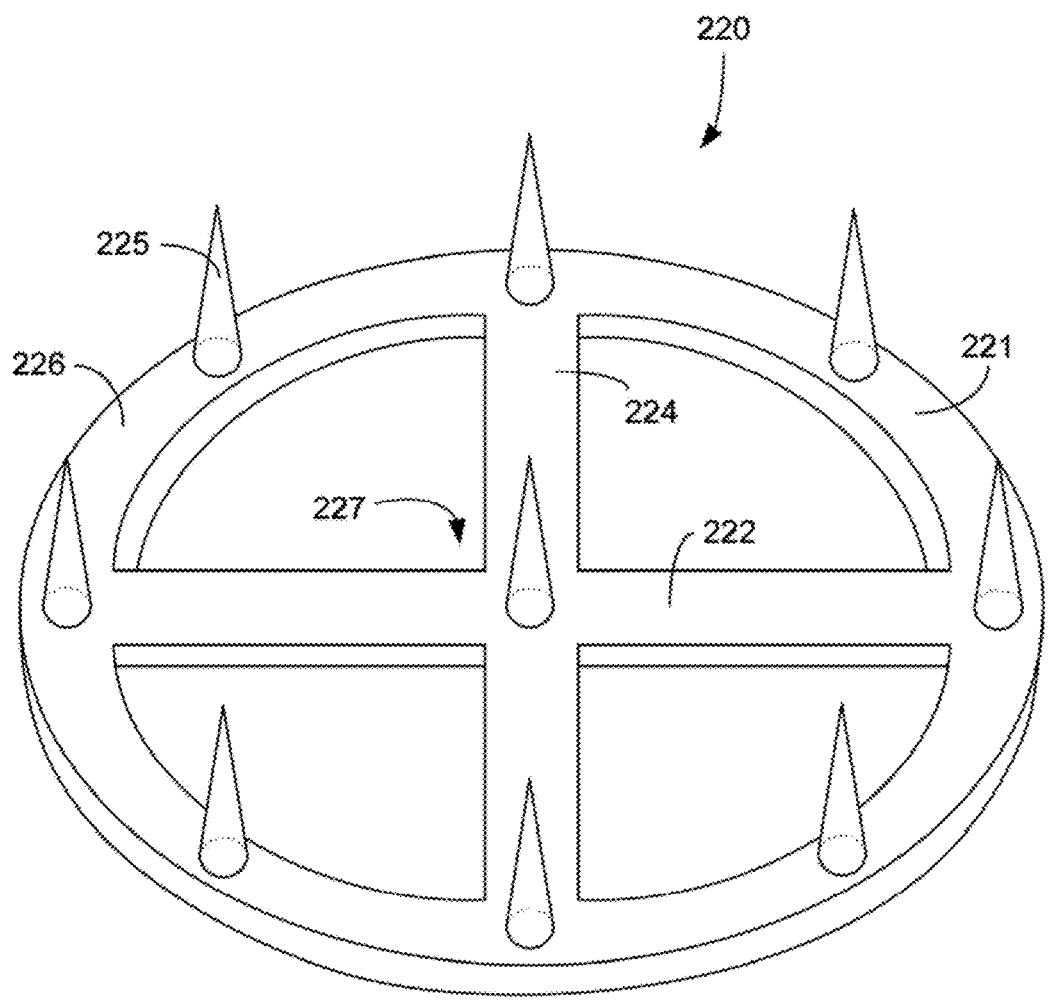
FIG. 5d is a perspective bottom view of the ionizing electrode shown in FIGS. 5a, 5b, and 5c.

FIGS. 3a through 3d illustrate a cross-shaped ionizing electrode 120 according to various embodiments. The cross-shaped ionizing electrode 120 may comprise a cross-shaped emitter plate 121 and five (5) emitter pins 125 connected to the emitter plate 121. The cross-shaped emitter plate 121 may comprise a first member 122 and a second member 124. The first member 122 and the second member 124 may intersect at a substantially 90-degree angle. The five (5) emitter pins 125 may be connected to a common side of the emitter plate 121, respectively positioned at the opposed ends of the first member 122, at the opposed ends of the second member 124, and at the intersection 127 of the first member 122 and the second member 124. FIG. 4 illustrates an ionizing electrode 120' comprising a cross-shaped emitter plate 121 and seven (7) emitter pins 125.

The ionizing electrodes 120/120' illustrated in FIGS. 3a through 4 may comprise through-holes 128 positioned at opposed ends of the second member 124. The through-holes 128 may be configured to mount the ionizing electrode 120 in relation to other components of a fluid charging system, such as, for example, a fluid vessel, a ground electrode, fluid sampling devices, support structures, and the like. The emitter plate 121 illustrated in FIGS. 3a through 4 may have a monolithic construction, the emitter plate 121 being formed from a single piece of material, such as, for example, a stainless steel. However, it is understood that in various embodiments, an emitter plate may comprise multiple discrete segments, such as, for example, first and second members, that may be metallurgically or mechanically joined together using techniques such as, for example, soldering, brazing, welding, and mechanical fastening.

FIGS. 5a through 5d illustrate an annular- and cross-shaped ionizing electrode 220 according to various embodiments. The annular- and cross-shaped ionizing electrode 220 comprises an annular- and cross-shaped emitter plate 221 and nine (9) emitter pins 225 connected to the emitter plate 221. The annular- and cross-shaped emitter plate 221 may comprise an annular member 226, a first linear member 222, and a second linear member 224. The first linear member 222 and the second linear member 224 may intersect at a substantially 90-degree angle to form a cross-shaped portion, and the cross-shaped portion intersects the annular member 226 at opposed ends of the first and second linear members 222 and 224. The nine (9) emitter pins 225 may be connected to a common side of the emitter plate 221, wherein eight (8) of the emitter pins may be positioned equidistant from each other around the annular member 226, and one (1) emitter pin may be positioned at the intersection 227 of the first member 222 and the second member 224.

The emitter plate 221 illustrated in FIGS. 5a through 5d may have a monolithic construction, the emitter plate 221 being formed from a single piece of material, such as, for example, a stainless steel. However, it is understood that in various embodiments, an emitter plate may comprise multiple discrete segments, such as, for example, an annular member and first and second linear members, that are metallurgically or mechanically joined together using techniques such as, for example, soldering, brazing, welding, and mechanical fastening.

In operation, electrical current delivered to the ionizing electrode concentrates at the tips of the emitter pins and ionizes atoms and/or molecules comprising the surrounding air or other gaseous atmosphere, producing an ion cloud. The ion cloud emits from the emitter pins and moves toward the ground electrode along a static electric field established between the ionizing electrode and the ground electrode in accordance with the physical principles of static electricity. This produces an ion field between the ionizing electrode and the ground electrode. The polarity of the ion field is the same as the polarity of the electrical current provided to the ionizing electrode. Although the ion fields illustrated in the figures presented herein are shown with a positive polarity (+) symbol, it is understood that, in various embodiments, the ion field may be of negative polarity. Materials contacting the ion field become charged at the same polarity as the ion field.

In various embodiments, a fluid vessel may be positioned between and adjacent to the electrodes so that the ion field contacts fluid contained within the fluid vessel, thereby charging the fluid. The emitter pins may be connected to the side of the emitter plate that faces an open top end of a fluid vessel, which facilitates contact between the field produced by the ionizing electrode and fluid contained in the fluid vessel to charge the fluid. Although the ionizing electrodes illustrated in certain figures presented herein are shown positioned adjacent an open top end of a fluid vessel, it is understood that, in various embodiments, the ionizing electrodes may be positioned adjacent to any region or end of an open or closed fluid vessel, provided the ionizing electrodes and ground electrodes are mutually positioned in a spaced apart relationship.

In various embodiments, the shape and dimensions of an emitter plate may be dependant upon the fluid charging system in which the ionizing electrode is to be employed. In various embodiments, the number, dimensions, and spatial orientation of emitter pins connected to an emitter plate may be dependant upon the fluid charging system in which the ionizing electrode is to be employed. For instance, larger fluid vessels containing larger volumes of fluid to be charged may require emitter plates having a larger vessel-facing surface area and/or a greater number of emitter pins to produce an ion field sufficient to charge the volume of fluid in the vessel. In addition, the shape and dimensions of an emitter plate may be controlled, at least in part, by the dimensions and spatial orientation of other components of a fluid charging system, such as, for example, the fluid vessel and fluid sampling devices. In various embodiments, a fluid charging system may comprise two or more discrete ionizing electrodes. Embodiments comprising a plurality of ionizing electrodes may be used with larger fluid vessels or multiple fluid vessels, for example.

In various embodiments, a ground electrode may be made of a conductive metallic material, such as, for example, aluminum or aluminum alloys. The shape and dimensions of a ground electrode may be dependant upon the fluid charging system in which the ground electrode is to be employed. In various embodiments, a ground electrode comprises a ground plate configured to seat and support a fluid vessel. For instance, a circular-shaped ground plate may have a diameter that substantially matches the diameter of a cylindrical fluid vessel.

In various embodiments, a fluid vessel may be made of a non-conductive material, such as, for example, plastic or glass. The fluid vessel may be made of non-conductive material in order to prevent a current from arcing from the ionizing electrode to the vessel, which could cause undesirable sparking. In addition, the presence of a conductive material between an ionizing electrode and a ground electrode may cause distortion of the static electric field between the electrodes, and distortion of the resulting ion field, which could prevent the charging of fluid in the vessel. Therefore, all additional system components adjacent to and between an ionizing electrode and a ground electrode (e.g., fluid sampling devices, support structures, and the like) may be made of non-conductive materials.

In various embodiments, an ionizing electrode may be connected to a high voltage electrical power source by a high voltage cable that delivers current from the high voltage electrical power source to the ionizing electrode. In various embodiments, a high voltage cable may connect a high voltage electrical power source to a resistor unit, and the resistor unit may be connected to an ionizing electrode via a high voltage electrical lead. In this manner, a resistor unit may be connected in series between a high voltage electrical power source and an ionizing electrode. A resistor unit decreases the amount of current delivered to the ionizing electrode by the high voltage power source, which may reduce the potential for sparking and provide for stable ionic emission.

Figure 6A:
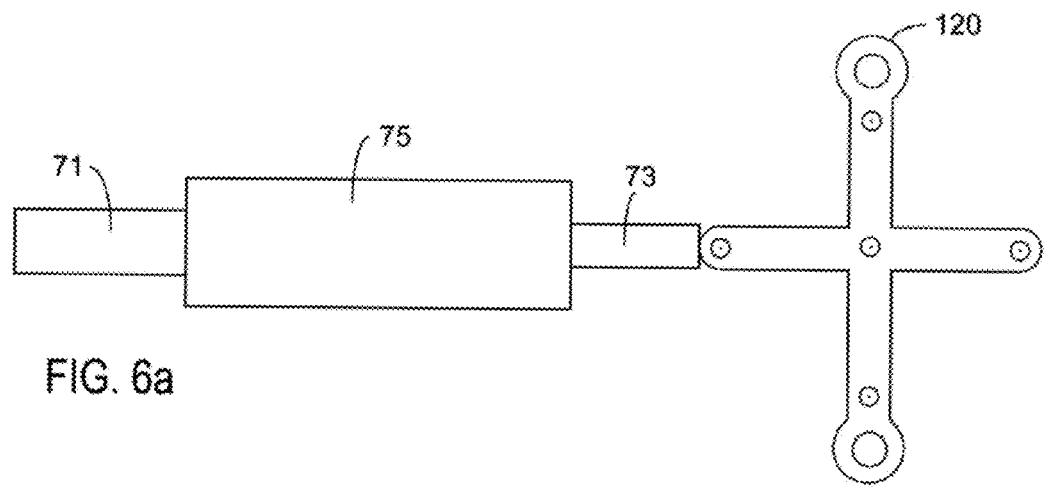
FIG. 6a is a bottom view of an assembly comprising the cross-shaped ionizing electrode shown in FIGS. 3a through 3d connected to a resistor unit.
Figure 6B:
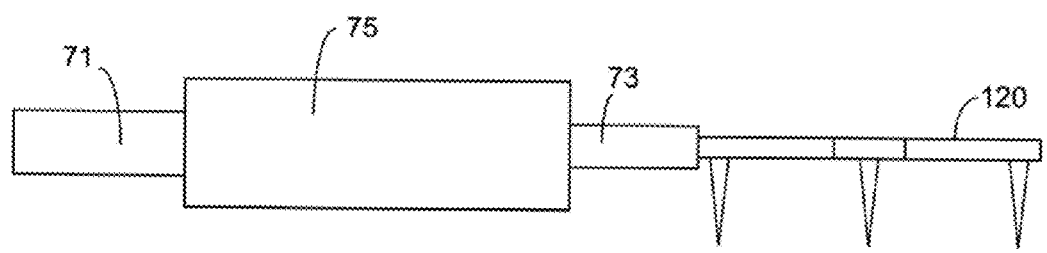
Figure 6C:
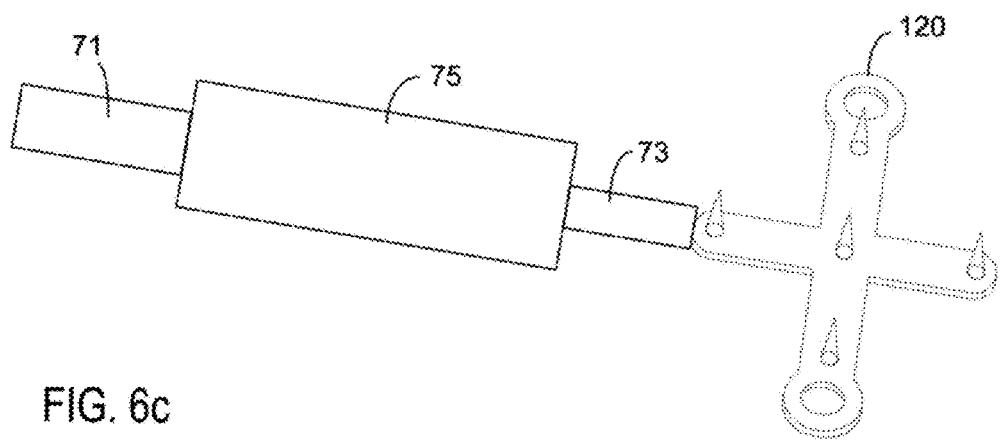
FIG. 6c is a perspective bottom view of the assembly shown in FIGS. 6a and 6b.
Figure 7A:
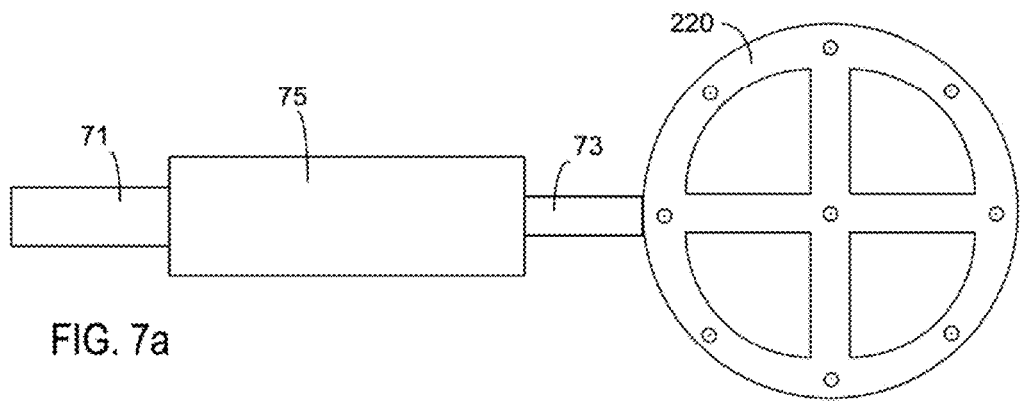
FIG. 7a is a bottom view of an assembly comprising the annular- and cross-shaped ionizing electrode shown in FIGS. 4a through 5d connected to a resistor unit.
Figure 7B:
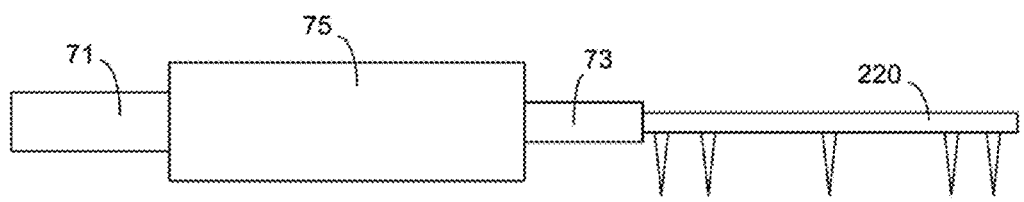
Figure 7C:
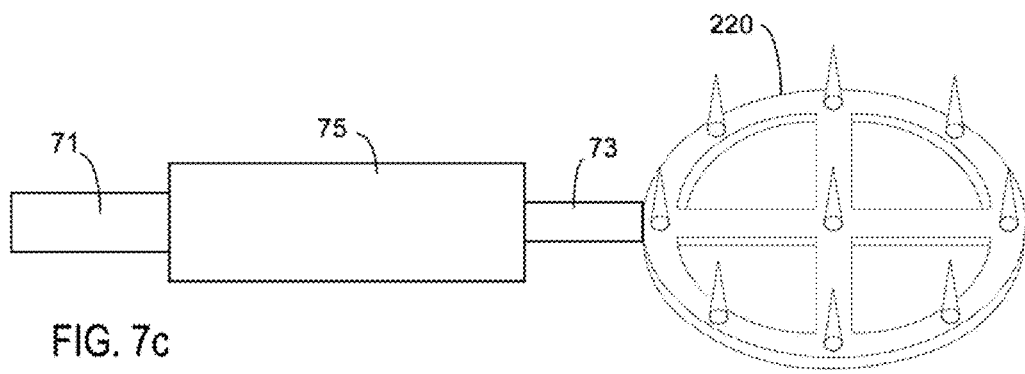
FIG. 7c is a perspective bottom view of the assembly shown in FIGS. 7a and 7b.

FIGS. 6a through 6c illustrate an assembly comprising a resistor unit 75 connected to an ionizing electrode 120 via a high voltage electrical lead 73 according to various embodiments. The resistor unit 75 may also be connected to a high voltage cable 71 that may connect the assembly to a high voltage electrical power source. In this manner, the resistor unit 75 may be connected in series between the high voltage electrical power source and the ionizing electrode 120. FIGS. 7a through 7c illustrate an assembly comprising a resistor unit 75 connected to an ionizing electrode 220 via a high voltage electrical lead 73 according to various embodiments. The resistor unit 75 may also be connected to a high voltage cable 71 that may connect the assembly to a high voltage electrical power source. In this manner, the resistor unit 75 may be connected in series between the high voltage electrical power source and the ionizing electrode 220.

Figure 8:
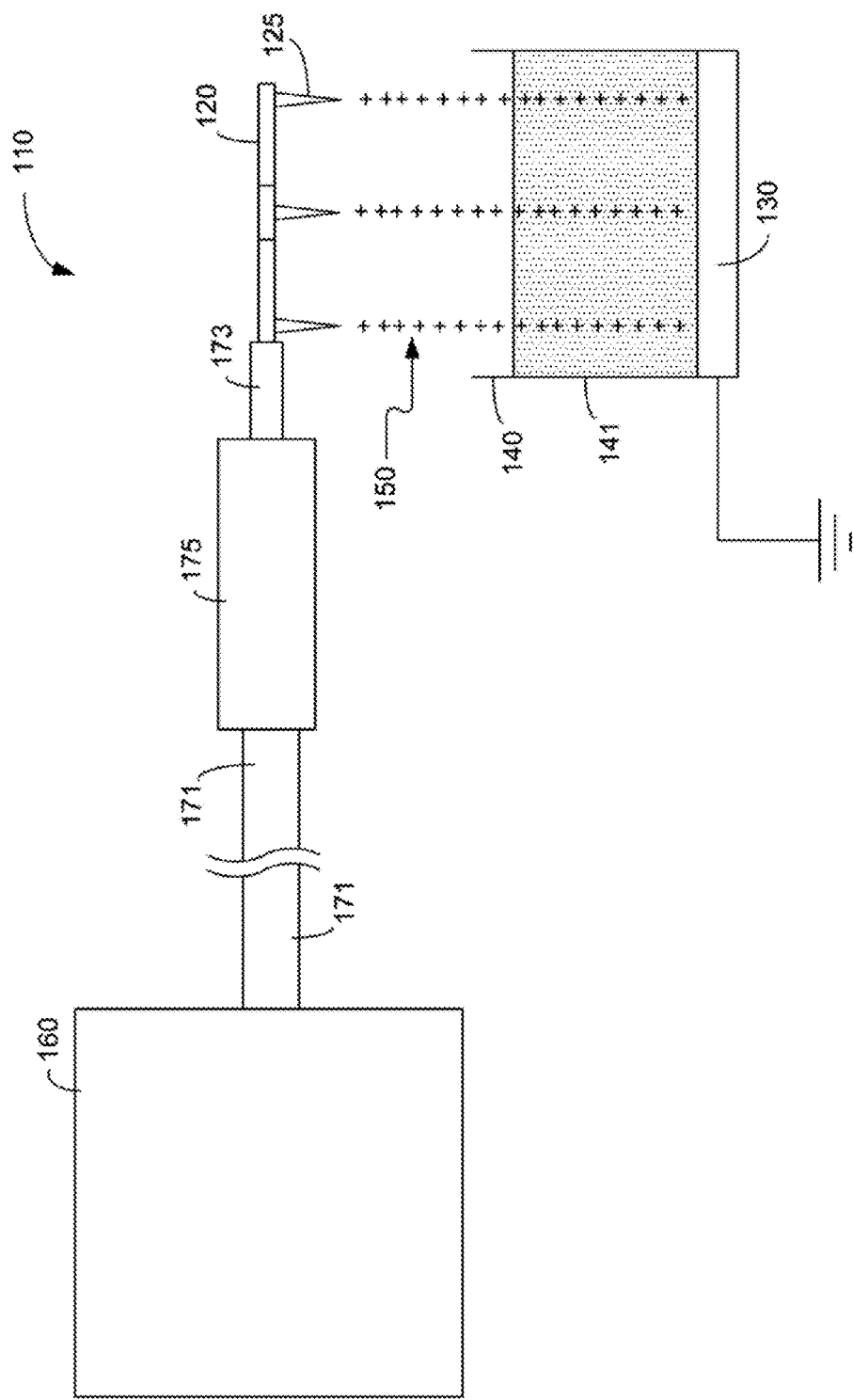
FIG. 8 is a side view schematic diagram of a fluid charging system comprising the assembly shown in FIGS. 6a through 6c, a ground electrode, and a fluid vessel positioned between an adjacent ionizing electrode and an adjacent ground electrode.

FIG. 8 illustrates a fluid charging system 110 according to various embodiments. The fluid charging system 110 comprises an ionizing electrode 120 positioned adjacent to a fluid vessel 140 and a ground electrode 130 positioned adjacent to the fluid vessel 140. The ionizing electrode 120 may be connected to an electrical power source 160 via a high voltage cable 171, a resistor unit 175, and a high voltage electrical lead 173. The ground electrode 130 may be electrically grounded relative to the ionizing electrode 120. The ionizing electrode 120 and the ground electrode 130 may produce an ion field 150 that contacts a fluid 141 contained in the fluid vessel 140, thereby charging the fluid 141. The ionizing electrode 120 and the ground electrode 130 may be opposed so that the fluid vessel is positioned between the ionizing electrode 120 and the ground electrode 140. The ionizing electrode 120 may be positioned adjacent to an open top end of the fluid vessel 140 with the emitter pins 125 facing the vessel, which facilitates contact between the ion field 150 and the fluid 141.

Figure 9:
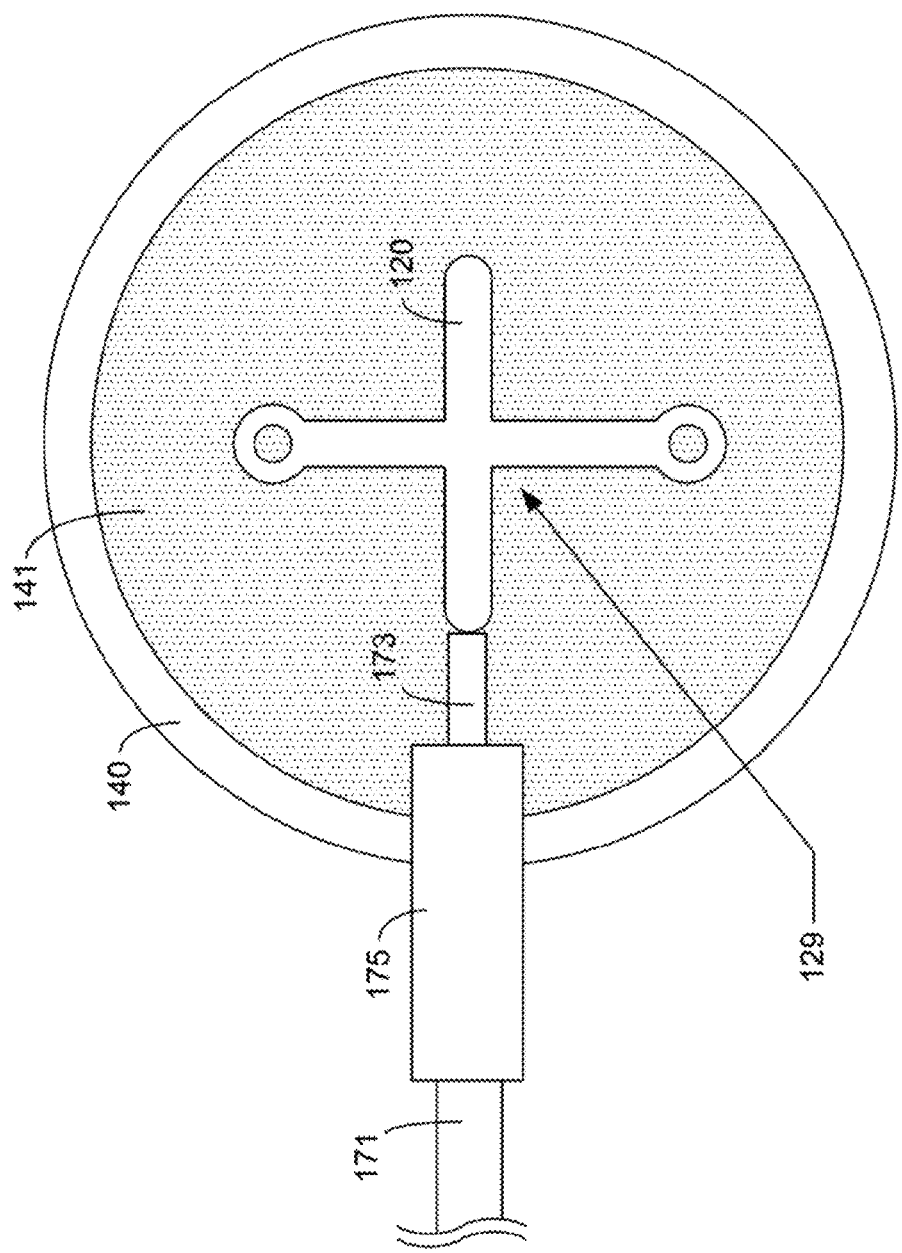
FIG. 9 is a top view schematic diagram of the assembly shown in FIGS. 6a through 6c positioned so that the ionizing electrode is adjacent to an open top end of a fluid vessel.

FIG. 8 schematically illustrates the vertical positioning of the ionizing electrode 120 relative to the fluid vessel 140. FIG. 9 schematically illustrates the horizontal positioning of the ionizing electrode 120 relative to the fluid vessel 140.

Figure 10:
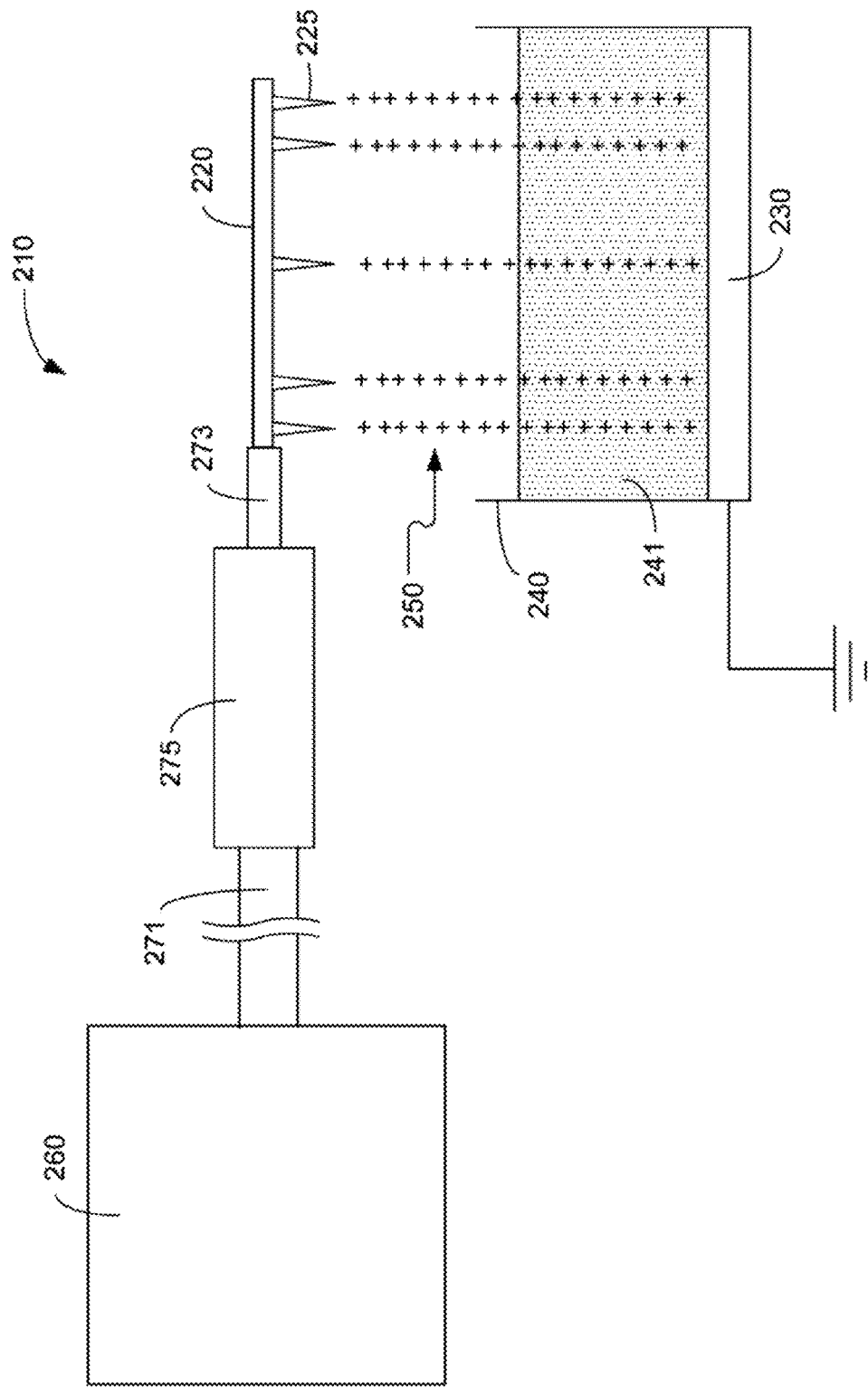
FIG. 10 is a side view schematic diagram of a fluid charging system comprising the assembly shown in FIGS. 7a through 7c, a ground electrode, and a fluid vessel positioned between an adjacent ionizing electrode and an adjacent ground electrode.

FIG. 10 illustrates a fluid charging system 210 according to various embodiments. The fluid charging system 210 may comprise an ionizing electrode 220 positioned adjacent to a fluid vessel 240 and a ground electrode 230 positioned adjacent to the fluid vessel 240. The ionizing electrode 220 may be connected to an electrical power source 260 via a high voltage cable 271, a resistor unit 275, and a high voltage electrical lead 273. The ground electrode 230 may be electrically grounded relative to the ionizing electrode 220. The ionizing electrode 220 and the ground electrode 230 produce an ion field 250 that contacts a fluid 241 contained in the fluid vessel 240, thereby charging the fluid 241. The ionizing electrode 220 and the ground electrode 230 may be opposed so that the fluid vessel is positioned between the ionizing electrode 220 and the ground electrode 240. The ionizing electrode 220 may be positioned adjacent to an open top end of the fluid vessel 240 with the emitter pins 225 facing the vessel, which facilitates contact between the ion field 250 and the fluid 241.

Figure 11:
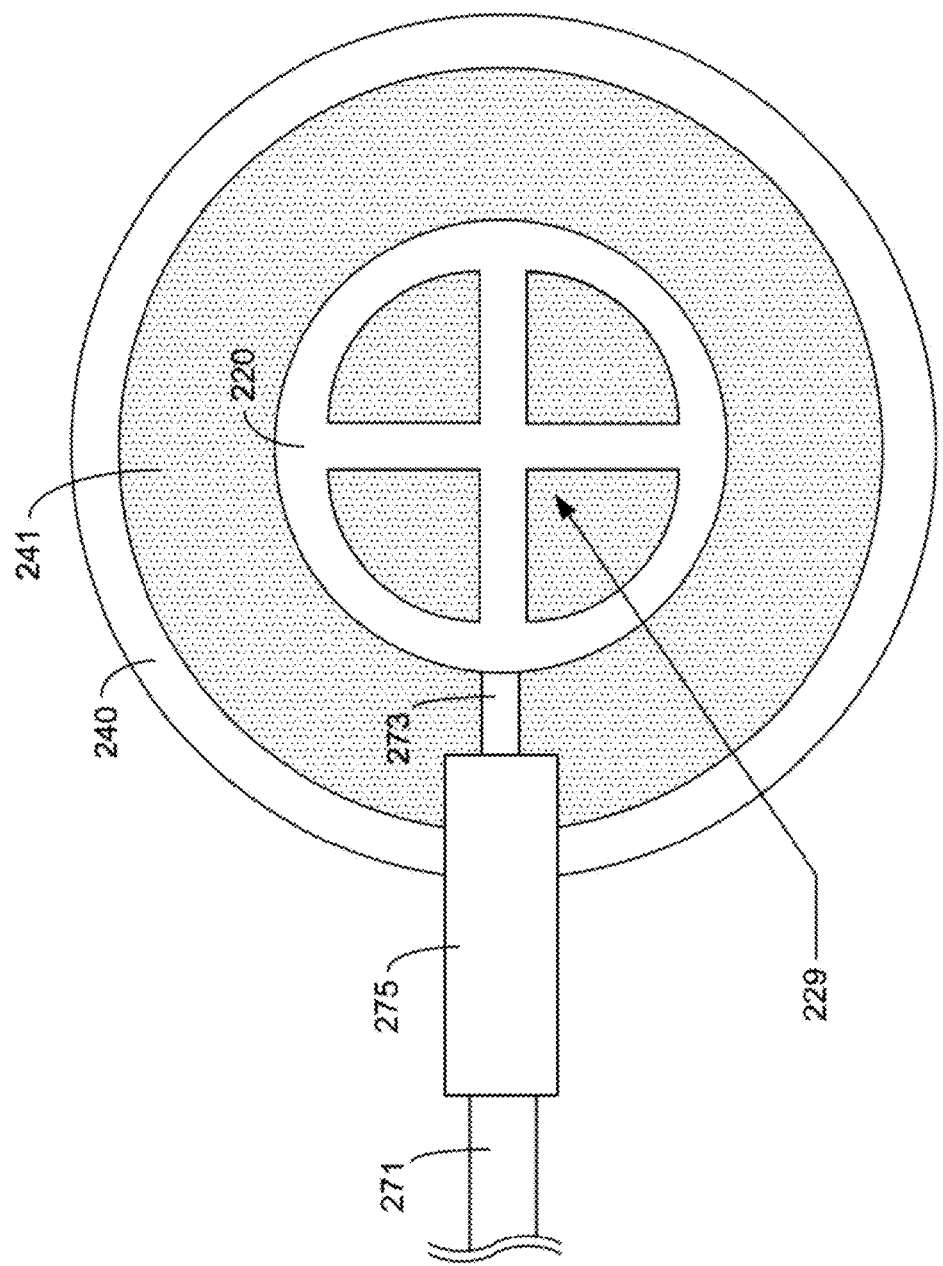
FIG. 11 is a top view schematic diagram of the assembly shown in FIGS. 7a through 7c positioned so that the ionizing electrode is adjacent to an open top end of a fluid vessel.

FIG. 10 schematically illustrates the vertical positioning of the ionizing electrode 220 relative to the fluid vessel 240. FIG. 11 schematically illustrates the horizontal positioning of the ionizing electrode 220 relative to the fluid vessel 240.

Figure 12:
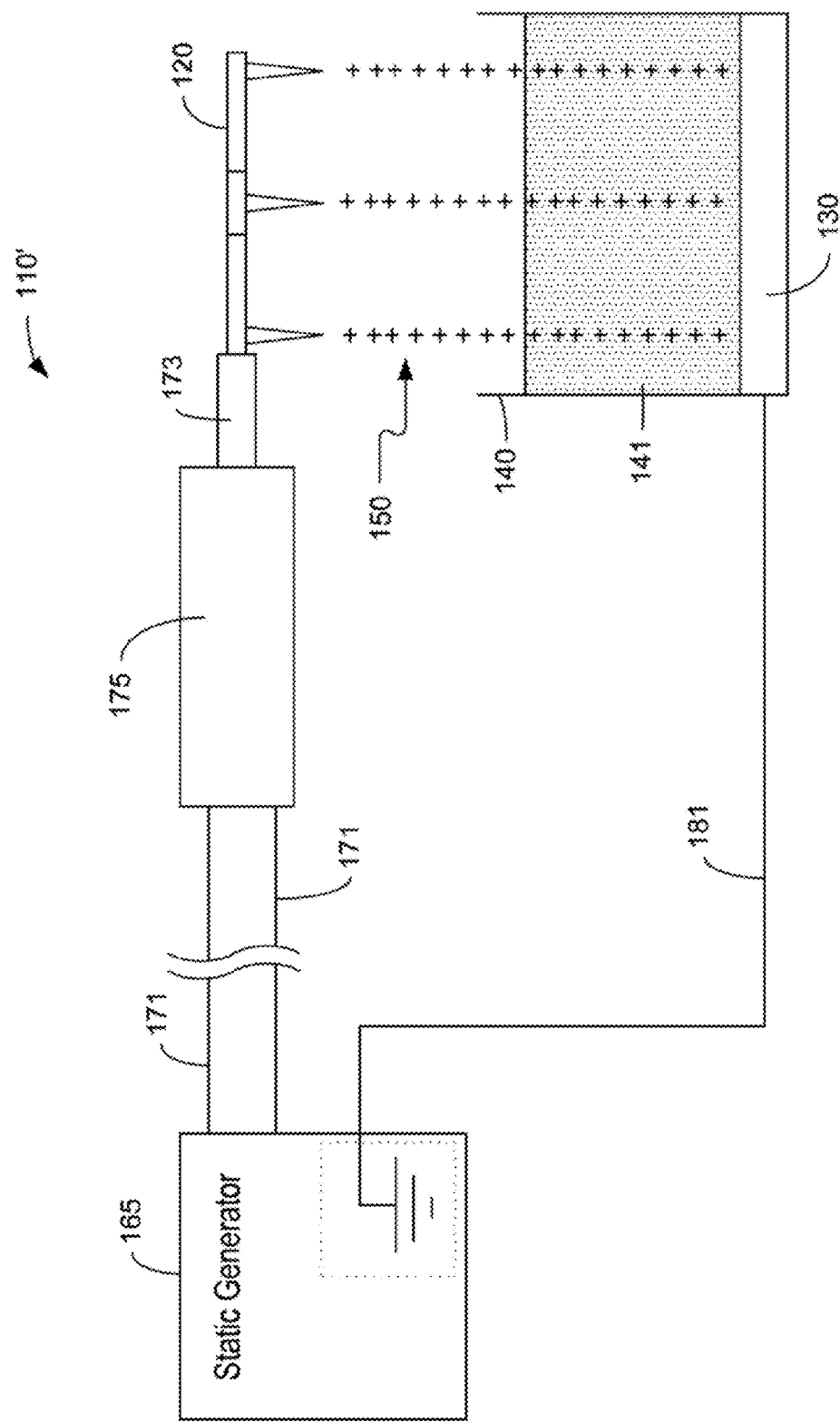
FIG. 12 is a side view schematic diagram of a fluid charging system comprising a static generator electrical power source.

In various embodiments, the electrical power source may comprise a static generator. Static generators provide stable and controllable current or voltage that may be used to produce an ion field using an ionizing electrode in accordance with the physical principles of static electricity. Examples of static generators that may find utility in various embodiments disclosed herein include the Fraser Model 7300 or Fraser Model 7330 static generators available from Fraser Anti-Static Techniques Ltd. (http://www.fraser-anti-static.co.uk/index.html). FIG. 12 illustrates a fluid charging system 110' similar to the fluid charging system 110 illustrated in FIG. 8. The fluid charging system 110' may comprise a static generator 165 that provides a current to ionizing electrode 120 to produce ion field 150. The ground electrode 130 may be connected to a ground lug on the static generator 165 via an electrical line 181.

Figure 13:
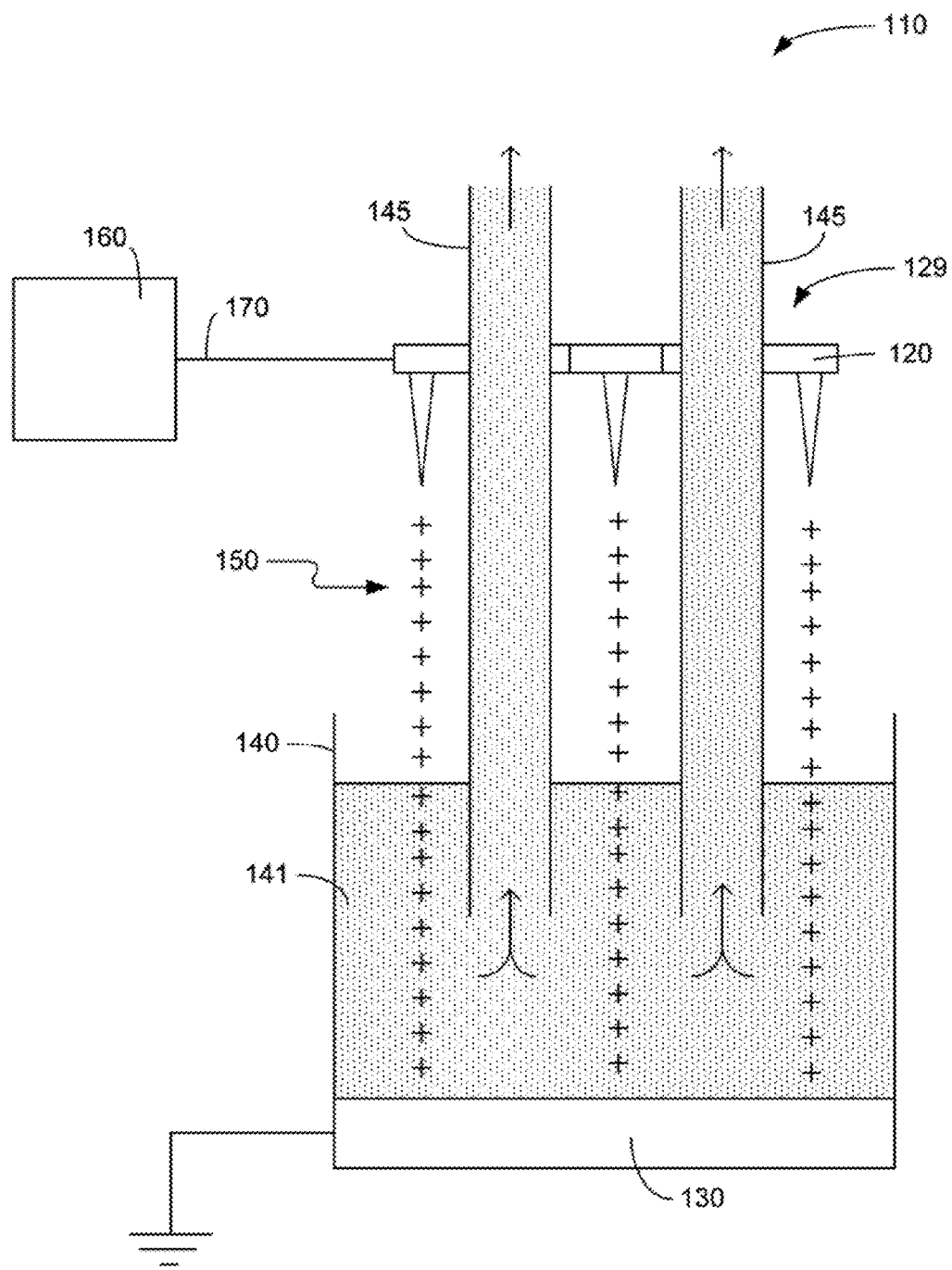
FIG. 13 is a side view schematic diagram of a fluid charging system comprising the cross-shaped ionizing electrode shown in FIGS. 3a through 3d and fluid sampling devices positioned through open quadrant regions of the emitter plate.
Figure 14:
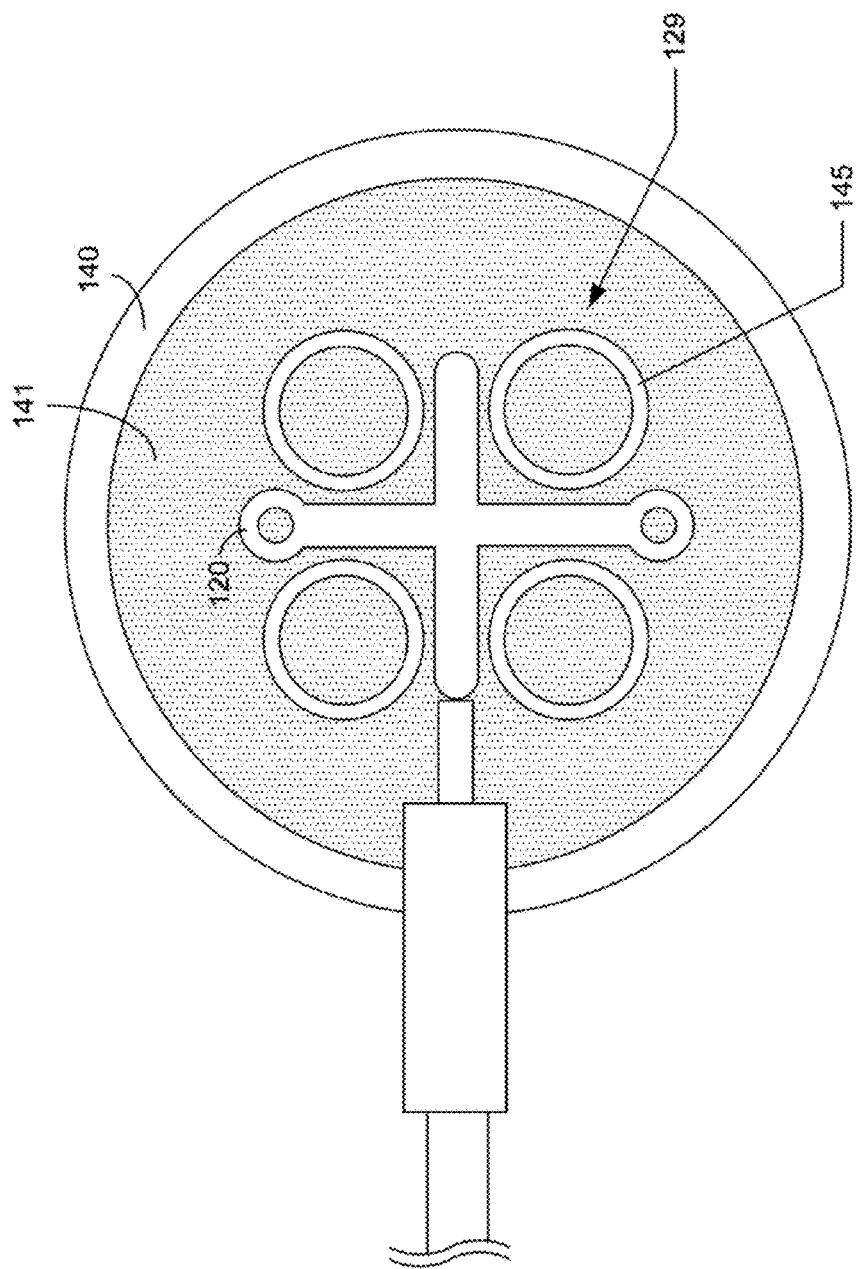
FIG. 14 is a top view schematic diagram of the assembly shown in FIGS. 6a through 6c positioned so that the ionizing electrode is positioned adjacent to an open top end of a fluid vessel and showing fluid sampling devices positioned through open quadrant regions of the emitter plate.
Figure 15:
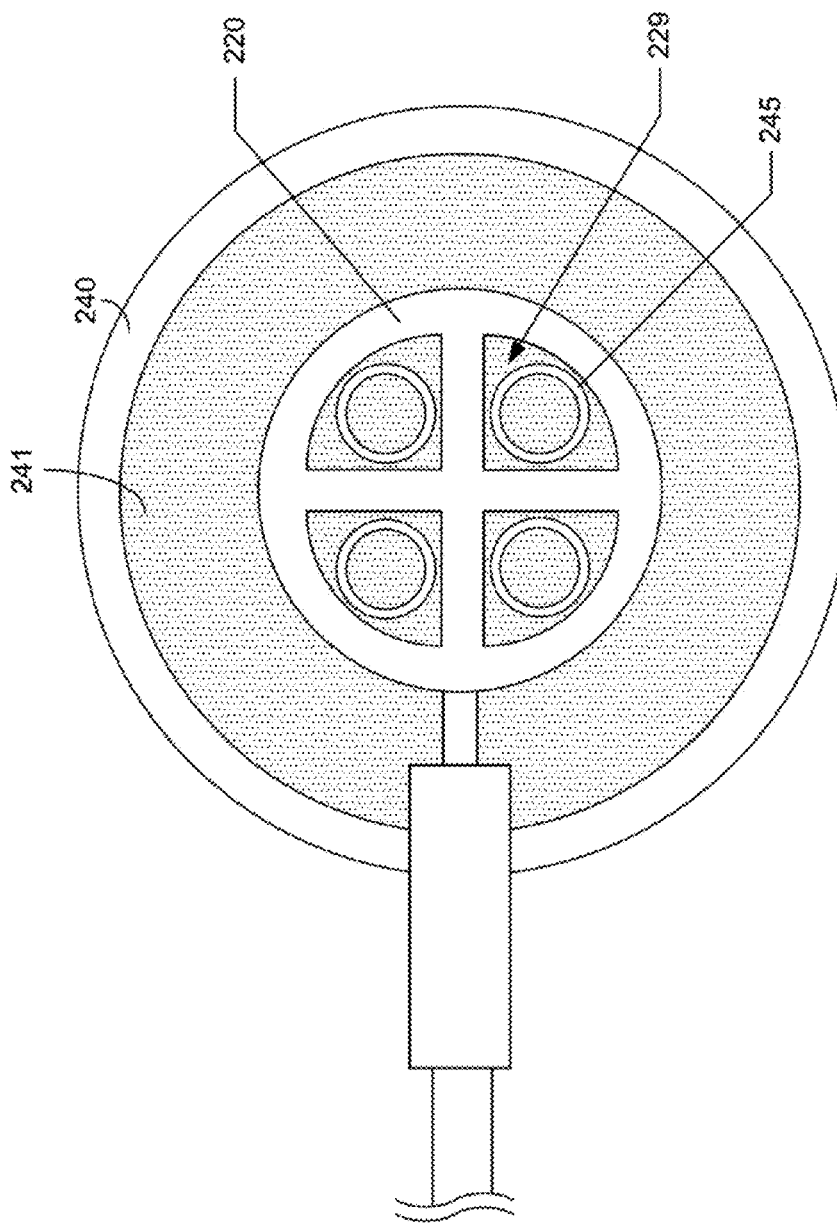
FIG. 15 is a top view schematic diagram of the assembly shown in FIGS. 7a through 7c positioned so that the ionizing electrode is positioned adjacent to an open top end of a fluid vessel and showing fluid sampling devices positioned through open quadrant regions of the emitter plate.

FIG. 13 illustrates a fluid charging system 110 comprising fluid sampling devices 145. The fluid sampling devices 145 may be configured to withdraw a fluid 141 from the fluid vessel 140, wherein the withdrawn fluid 141 has been charged by the ion field 150. The fluid sampling devices 145 may comprise tubes in fluid communication with the fluid vessel 140. As illustrated in FIG. 14, the fluid sampling devices 145 may be positioned through open quadrant regions 129 of the emitter plate portion of the cross-shaped ionizing electrode 120. FIG. 15 shows analogous fluid sampling devices 245 positioned through open quadrant regions 229 of an emitter plate portion of an annular- and cross-shaped ionizing electrode 220.

Figure 16:
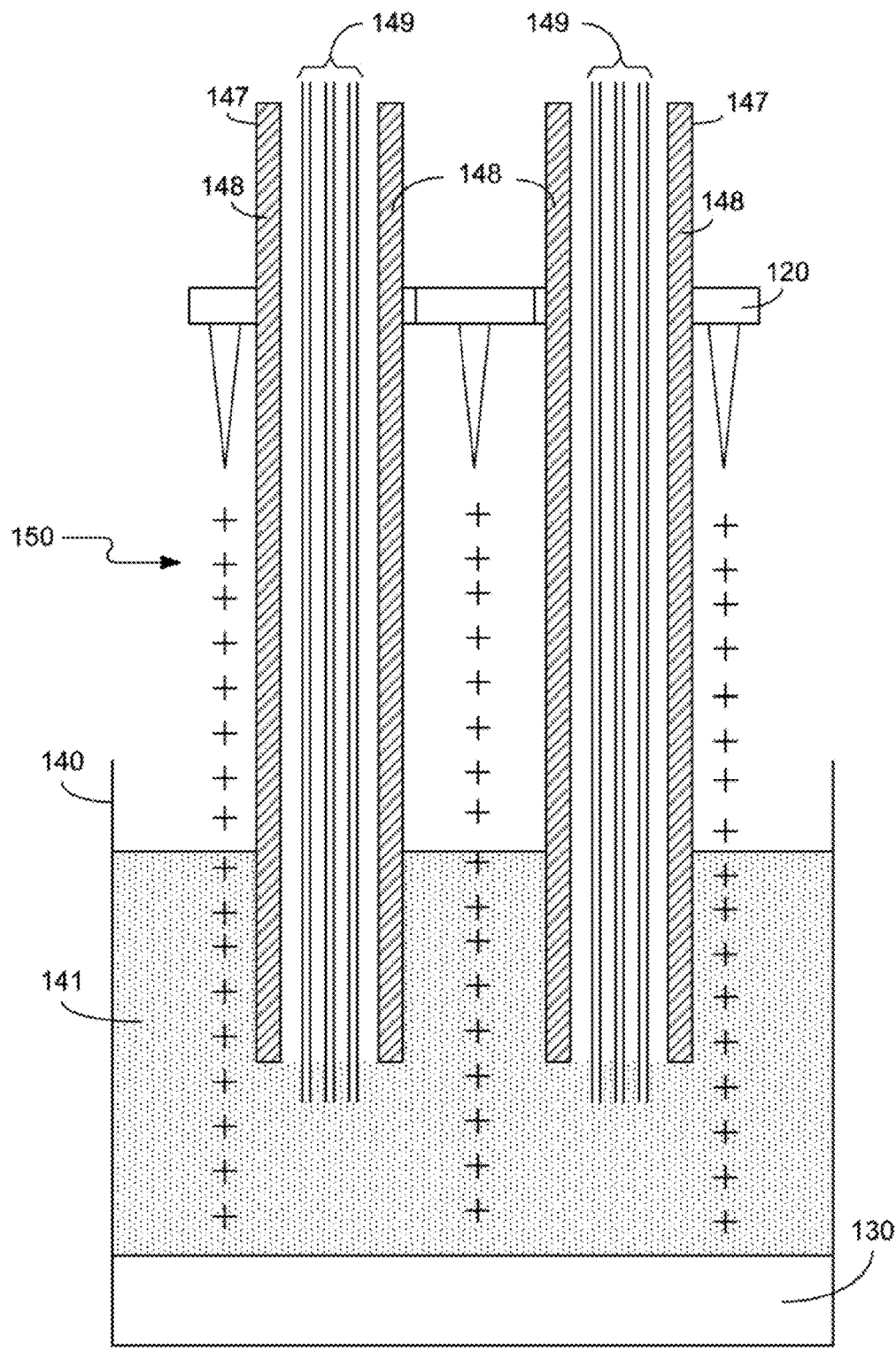
FIG. 16 is a side view schematic diagram of a fluid charging system comprising the cross-shaped ionizing electrode shown in FIGS. 3a through 3d and fluid sampling devices positioned through open quadrant regions of the emitter plate.
Figure 17:
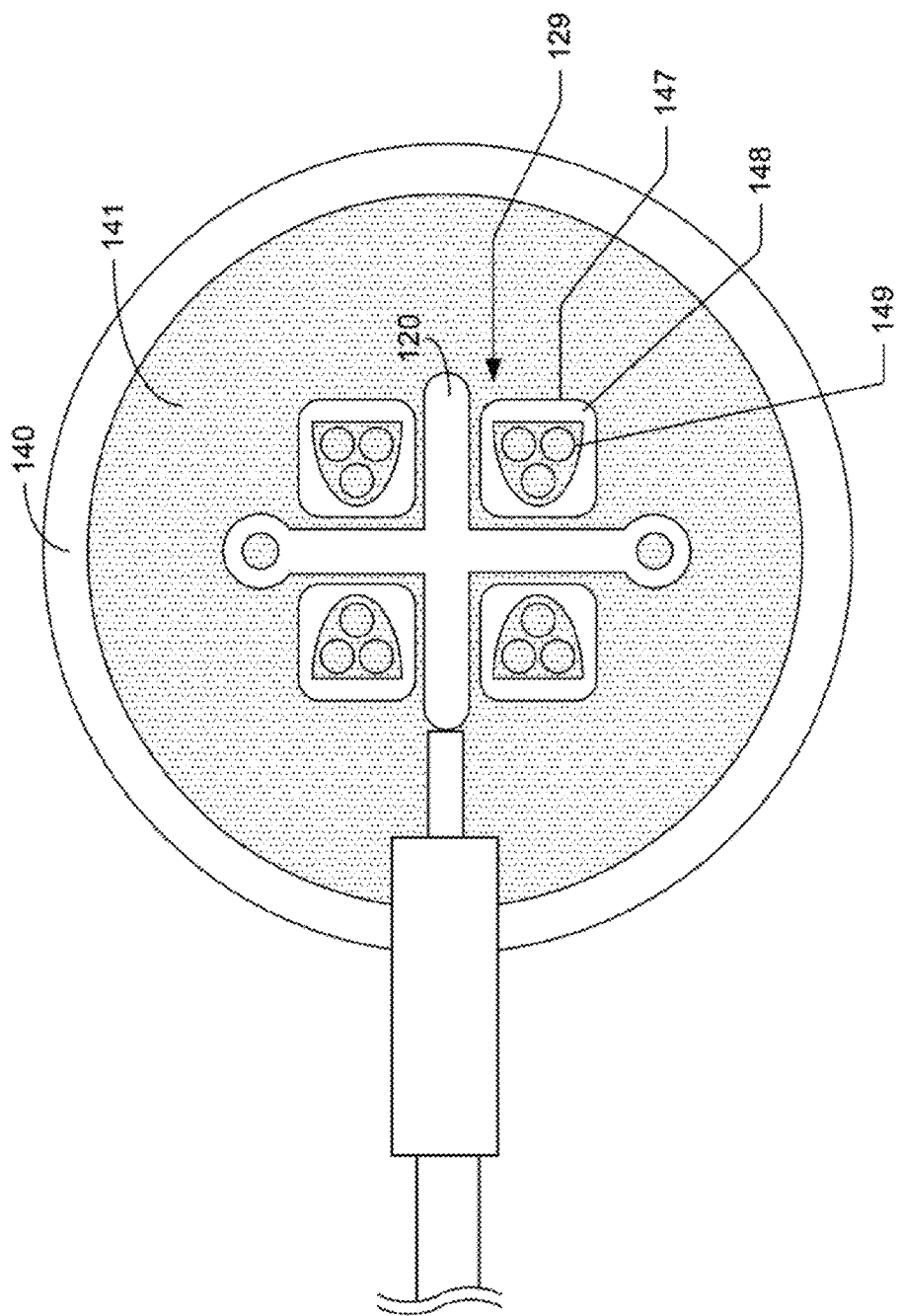
FIG. 17 is a top view schematic diagram of the assembly shown in FIGS. 6a through 6c positioned so that the ionizing electrode is positioned adjacent to an open top end of a fluid vessel and showing fluid sampling devices positioned through open quadrant regions of the emitter plate.

FIG. 16 illustrates a fluid charging system comprising fluid sampling devices 147. The fluid sampling devices 147 may be configured to withdraw a fluid 141 from the fluid vessel 140, wherein the withdrawn fluid 141 has been charged by the ion field 150. The fluid sampling devices 147 may comprise sheaths 148 surrounding a plurality of tubes 149 in fluid communication with the fluid vessel 140. As illustrated in FIG. 17, the fluid sampling devices 147 may be positioned through open quadrant regions 129 of the emitter plate portion of the cross-shaped ionizing electrode 120. The fluid sampling devices 147 may comprise fluid sampling devices such as, for example, the devices described in United States Patent Application Publication Nos. 2010/0304443 and 2010/0294048, which are incorporated by reference herein.

Figure 18:
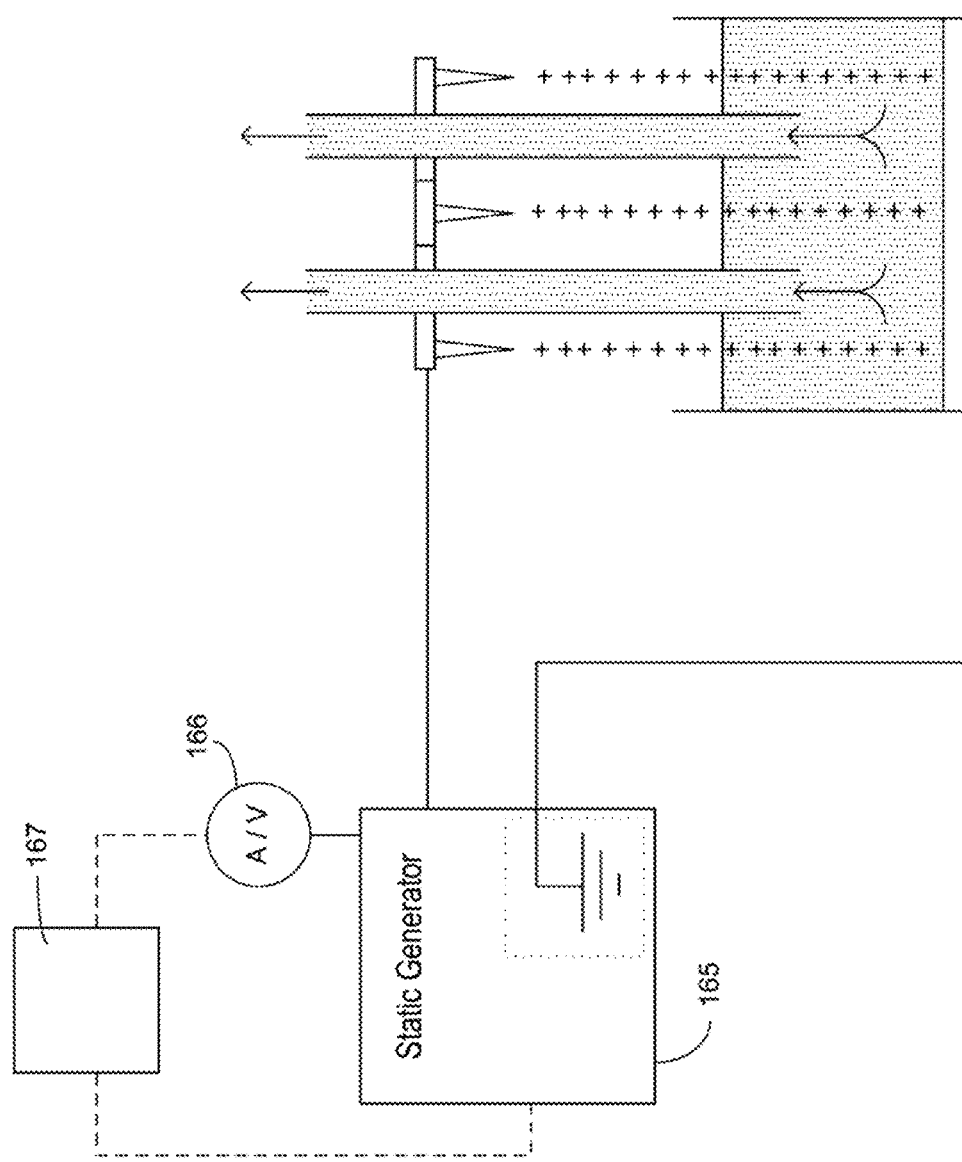
FIG. 18 is a side view schematic diagram of a fluid charging system comprising a static generator and a controller.

In various embodiments, a fluid charging system may comprise a controller to control the current and/or voltage output of an electrical power source, such as, for example, a static generator. The controller may comprise hardware, software, or a combination of hardware and software configured to control the current and/or voltage output of an electrical power source so that a stable ion field charges fluid contained in a fluid vessel positioned between a ground electrode and an ionizing electrode connected to the current and/or voltage output of the electrical power source. FIG. 18 illustrates a fluid charging system comprising a controller 167 interfacing with a static generator 165. The voltage and/or current output of the static generator 165 may be measured at 166 and sent as an output signal to the controller 167. Based on the measured current and/or voltage, the controller 167 may send an input signal to the static generator 165 to adjust the current and/or voltage output to the ionizing electrode.

Although not shown in FIG. 18, other system parameters may be measured and used by the controller 167 to control the current and/or voltage output of the static generator or other electrical power source. For instance, current and/or voltage may be measured at other locations within the system and used by the controller 167. Further, fluid dynamic parameters, such as, for example, the fluid volume in a vessel, fluid flow rates, and/or fluid pressures, may be measured and used to control the current and/or voltage output of the static generator or other electrical power source in order to provide an effective ion field to charge fluid in accordance with the embodiments disclosed herein.

Figure 19:
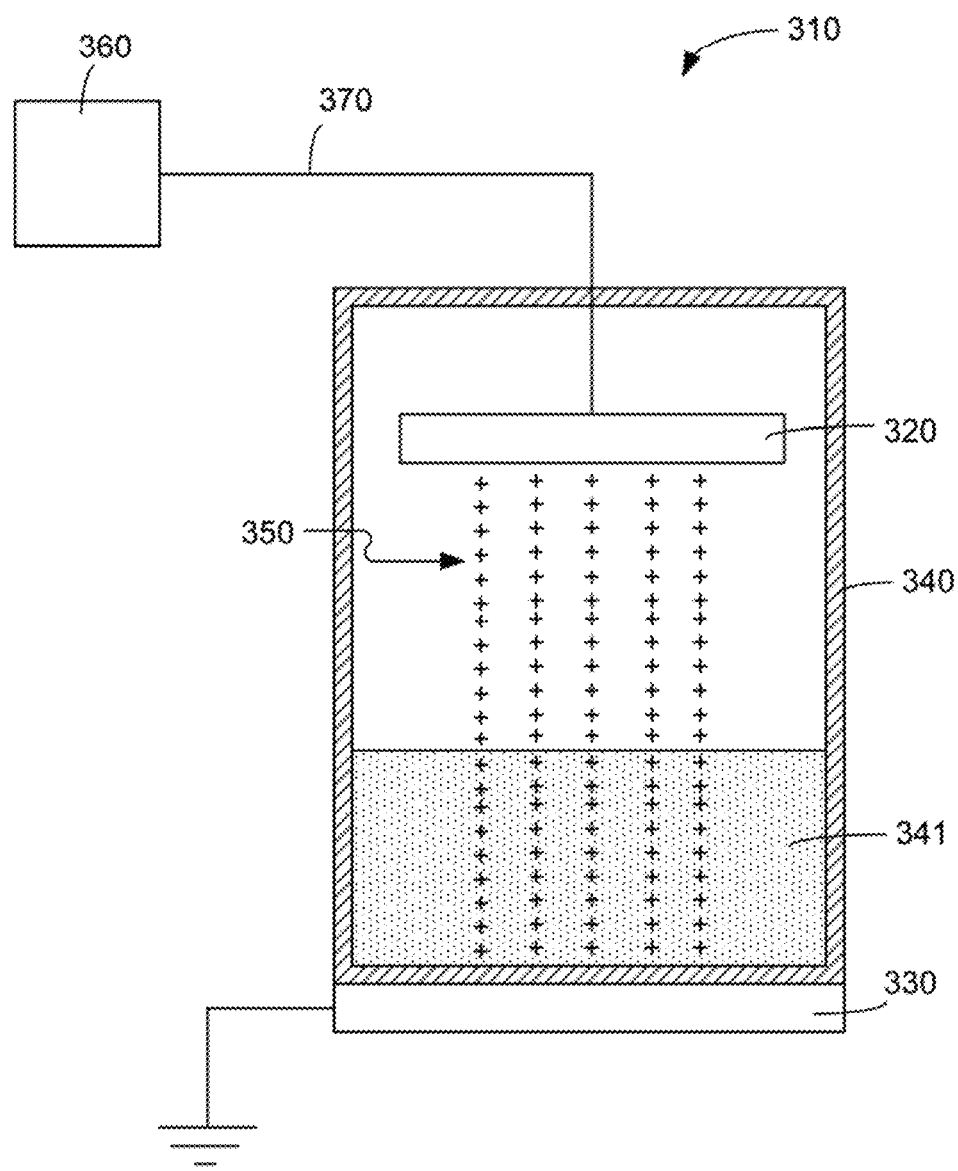
FIG. 19 is a side view schematic diagram of a fluid charging system comprising a closed fluid vessel, an ionizing electrode positioned inside and adjacent to the fluid vessel, and a ground electrode positioned outside and adjacent to the fluid vessel.

In various embodiments, the fluid charging systems disclosed herein may comprise a closed fluid vessel. FIG. 19 illustrates a fluid charging system 310 according to various embodiments. The fluid charging system 310 may comprise an ionizing electrode 320 positioned inside and adjacent to a closed fluid vessel 340. A ground electrode 330 may be positioned outside and adjacent to the fluid vessel 340. The ionizing electrode 320 may be connected to an electrical power source 360 via an electrical line 370. The ground electrode 330 may be grounded relative to the ionizing electrode 320 as indicated at 380. The ionizing electrode 320 and the ground electrode 330 produce an ion field 350 that contacts fluid 341 contained in the fluid vessel 340, thereby charging the fluid 341. The ionizing electrode 320 and the ground electrode 330 may be opposed so that the fluid vessel is positioned between the ionizing electrode 320 and the ground electrode 340. The fluid charging system 310 may also comprise fluid sampling devices (not shown).

Although the fluid vessels described herein have been illustrated without fluid communication ports, it is understood that in various embodiments the fluid charging systems disclosed herein may comprise open or closed fluid vessels comprising inlet and/or outlet ports in addition to, or instead of, the fluid sampling devices. For example, a fluid vessel may comprise one or more inlet ports for adding fluid to the fluid vessel to replace charged fluid that has been withdrawn by a fluid sampling device. In various embodiments, the flow rate of fluid added to the fluid vessel may be equal to the flow rate of fluid withdrawn from the fluid vessel. In this manner, the fluid vessel may function as a charging reservoir that contains a steady-state level of fluid. A fluid vessel may also comprise one or more outlet or drain ports for removing fluid from the fluid vessel.

In various embodiments, a fluid sampling device may be in fluid communication with a fluid dispensing device configured to dispense charged and/or mixed fluids to vessels, such as, for example, eppendorf tubes, vials, beakers, flasks, centrifuge tubes, capillary tubes, cryogenic vials, bags, channels, cups, containers, microtiter plates, microcards, and the like. The transport of charged fluids from the fluid vessel to other vessels may be accomplished, for example, using pumps, hydrostatic pressure, capillary forces, and the like.

In various embodiments, the fluid charging systems disclosed herein may be used to provide charged fluid to microfluidic processing networks and systems. A charged fluid may be mixed with other fluids in a microfluidic processing network or system. Microfluidic processing networks and systems in which fluids may be mixed are described, for example, in United States Patent Application Publication Nos. 2005/0092681, 2005/0272144, 2008/0277494, 2010/0015606, 2010/0029512, 2010/0109320, and 2010/0297748, which are all incorporated by reference herein. The fluid charging systems disclosed herein may be in fluid communication with microfluidic processing networks and systems such as those described in these documents.

In various embodiments, the fluid charging systems disclosed herein may be used to provide charged fluid to microfluidic processing networks and systems comprising liquid bridges. United States Patent Application Publication Nos. 2008/0277494, 2010/0015606, 2010/0029512, 2010/0109320, and 2010/0297748, which are all incorporated by reference herein, describe microfluidic processing networks and systems comprising liquid bridges. A liquid bridge is a device in which liquid droplets are formed. The droplets formed in a liquid bridge are enveloped in an immiscible carrier fluid. Generally, a liquid bridge is formed by an inlet in communication with a chamber that is filled with immiscible carrier fluid. The carrier fluid is immiscible with fluid droplets flowing through the inlet into the chamber. The fluid droplets expand until they are large enough to span a spatial gap between the inlet and an outlet in communication with the chamber. Droplet formation is accomplished, for example, by adjusting flow rate or by joining one or more additional fluid droplets to a first fluid droplet, resulting in formation of an unstable liquid bridge between the inlet and the outlet that subsequently ruptures from the inlet. After rupturing from the inlet, the fluid droplet enters the outlet, surrounded by the carrier fluid from the chamber. In some embodiments, the liquid bridge creates a droplet and also merges that droplet with other droplets in the liquid bridge. In some embodiments, droplets are formed using the autosampler previously described. After the droplet is formed, it may be then carried to the liquid bridge where it is then combined with other droplets, such as for example master mix, sample, or any other suitable fluid droplet.

The fluid charging systems disclosed herein may be configured to provide charged fluid to a liquid bridge. For example, a fluid sampling device of a fluid charging system may be in fluid communication with a liquid bridge. In various embodiments, a liquid bridge may be configured to segment a charged fluid into droplets. In various embodiments, a liquid bridge may be configured to mix droplets of charged fluid with droplet of other fluid (that may be uncharged or charged, for example, as described herein) that is miscible with the charged fluid. As used herein, the term "droplet" refers to a relatively small microfluidic quantity or plug of liquid as it is suspended and/or flows in an immiscible carrier liquid in a conduit or chamber, such as, for example, in a microfluidic processing network or system.

In various embodiments, a liquid bridge configured to segment charged fluid withdrawn from a fluid vessel into droplets comprises a first inlet port in fluid communication with a fluid sampling device, a second inlet port in fluid communication with a source of immiscible fluid, an outlet port, and a chamber. The inlet ports and the outlet port open into the chamber and may be structured and positioned so that fluid instability in fluid droplets formed between the first inlet port and the outlet port segments the fluid withdrawn from the fluid vessel into fluid droplets separated by the immiscible fluid. The fluid droplets may be withdrawn from the chamber through the outlet port.

In various embodiments, a liquid bridge configured to mix charged fluid withdrawn from a fluid vessel in a fluid charging system with one or more additional fluids that may be miscible with the charged fluid comprises a first inlet port in fluid communication with the fluid sampling device, one or more additional inlet ports in fluid communication with sources of the one or more additional fluids, an outlet port, and a chamber. The inlet ports and the outlet port open into the chamber and may be structured and positioned so that first fluid droplets formed at the first inlet port contact and mix with one or more additional fluid droplets formed at the one or more additional inlet ports, thereby forming unstable funicular bridges of mixed fluid. The unstable funicular bridges rupture, thereby forming mixed fluid droplets separated by immiscible carrier fluid that are withdrawn from the chamber through the outlet port. The net charge carried by the fluid withdrawn from the fluid vessel improves the mixing of the charged fluid with the one or more additional fluids.

In various embodiments, a liquid bridge configured to mix charged fluid withdrawn from a fluid vessel in a fluid charging system with one or more additional fluids that are miscible with the charged fluid comprises a chamber, one or more inlet ports, a first outlet port, and a second outlet port. The inlet ports and the outlet ports may open into the chamber. An inlet port may be in fluid communication with a fluid sampling device and sources of one or more additional fluids. The inlet ports may serially provide fluid droplets of the charged fluid withdrawn from the fluid vessel and the one or more additional fluids, wherein the droplets may be separated by an immiscible carrier fluid. The first outlet port may be configured to withdraw a portion of the immiscible carrier fluid entering the chamber. The inlet ports and the outlet ports may be structured and positioned so that trailing droplet transporting through the inlet port contact and mix with leading droplets formed at the inlet port in the chamber, thereby forming mixed fluid droplets that may be withdrawn from the chamber through the second outlet port separated by immiscible carrier fluid. The net charge carried by the fluid withdrawn from the fluid vessel improves the mixing of the charged fluid with the one or more additional fluids.

Further description of the structure and operation of segmenting liquid bridges and mixing liquid bridges is presented in United States Patent Application Publication Nos. 2008/0277494 and 2010/0029512, which are incorporated by reference herein.

In various embodiments, the fluid charging systems and methods disclosed herein may be used to mix reagents for a polymerase chain reaction (PCR) process, such as, for example, a quantitative PCR (Q-PCR) process, a digital PCR (dPCR) process, or a genotyping PCR (gPCR) process. PCR is a technique for the amplification of DNA samples. Q-PCR, for example, is a variant of PCR in which the amplification of DNA samples can be quantified to obtain data on the amount of DNA in a sample. A typical PCR reaction, such as, for example, a Q-PCR, dPCR, or gPCR reaction, contains reactants including: fluorescent double-stranded binding dye; Taq polymerase; deoxynucleotides of type A, C, G, and T; magnesium chloride; forward and reverse primers; and subject DNA. These reactants are all suspended within an aqueous fluid buffer. Reactants, however, may be assigned into two broad groups: universal reactants and reaction-specific reactants. Universal reactants are those common to most PCR reaction, and include: fluorescent double-stranded binding dye; Taq polymerase; deoxynucleotides A, C, G, and T; and magnesium chloride. Reaction-specific reactants include the forward and reverse primers and subject DNA. In various applications, it may be desirable to mix microfluidic quantities of universal reactants and reaction-specific reactants.

In various embodiments, a master mixture of universal PCR reactants may be charged using a fluid charging device, system, or method as disclosed herein. A fluid vessel in a fluid charging system may contain a master mixture of universal PCR reactants. A fluid sampling device may withdraw charged master mixture fluid. The charged master mixture fluid may be mixed in a downstream operation with one or more additional fluids comprising samples and/or reaction-specific reactants. For example, a mixing liquid bridge or other mixing microfluidic system may be in fluid communication with a fluid sampling device configured to withdraw charged master mixture and in fluid communication with a source of fluid comprising reaction-specific reactants. The net charge carried by the master mixture may improve the mixing of the master mixture with the fluid, thereby achieving a more homogeneous suspension of universal and reaction-specific PCR reactants in an aqueous buffer fluid.

In various embodiments, a fluid sampling device may be in fluid communication with a vessel, conduit, or channel in a thermal cycler device for performing amplification reactions according to a PCR technique. In various embodiments, a fluid sampling device may be in fluid communication with a thermal cycler device configured to perform continuous-flow PCR, such as, for example, the devices described in United States Patent Application Publication Nos. 2008/0280331, 2010/009273, 2010/0092987, and 2010/0304446, which are all incorporated by reference herein. In various embodiments, the fluid communication between a fluid sampling device and a vessel or conduit in a thermal cycler device may be provided by a microfluidic processing network or system, which may comprise one or more liquid bridges.

Liquid bridge systems can be fluidly connected, e.g., by tubes or channels, to any type of analysis device. In various embodiments, a liquid bridge microfluidic system connects a fluid charging system to a thermal cyler to perform PCR reactions on a DNA sample. An exemplary thermal cycler and methods of fluidly connecting a thermal cycler to a liquid bridge system are described in International Patent Application Publications Nos. WO 2005/023427, WO 2007/091230, and WO 2008/038259, which are incorporated by reference herein. A thermal cycler may be connected to an optical detecting device to detect the products of a PCR reaction. An optical detecting device and methods for connecting the device to the thermal cycler are described in International Patent Application Publications Nos. WO 2007/091230 and WO 2008/038259, which are incorporated by reference herein.

Further provided herein is a method of mixing droplets using electrostatic charging of droplets. In some embodiments a charged droplet, for example a statically charged droplet, may be directed toward a second droplet. The second droplet may be charged or uncharged. As the charged droplet approaches the second droplet, the charged droplet may induce charge separation, or further induce charge separation, in the awaiting second droplet. The charge separation may then cause the charged droplet and the second charged or uncharged droplet to become more attracted to each other and thereby may facilitate the combining of the two droplets. Additionally, the charge separation induced in the second droplet, together with the charge of the charged droplet may cause the two droplets to mix in a more efficient manner than when both droplets are uncharged. In some embodiments, a charged droplet may be combined with at least two droplets, which may be charged or uncharged, to form a charged droplet.

EXAMPLES

Example 1

Figure 20:
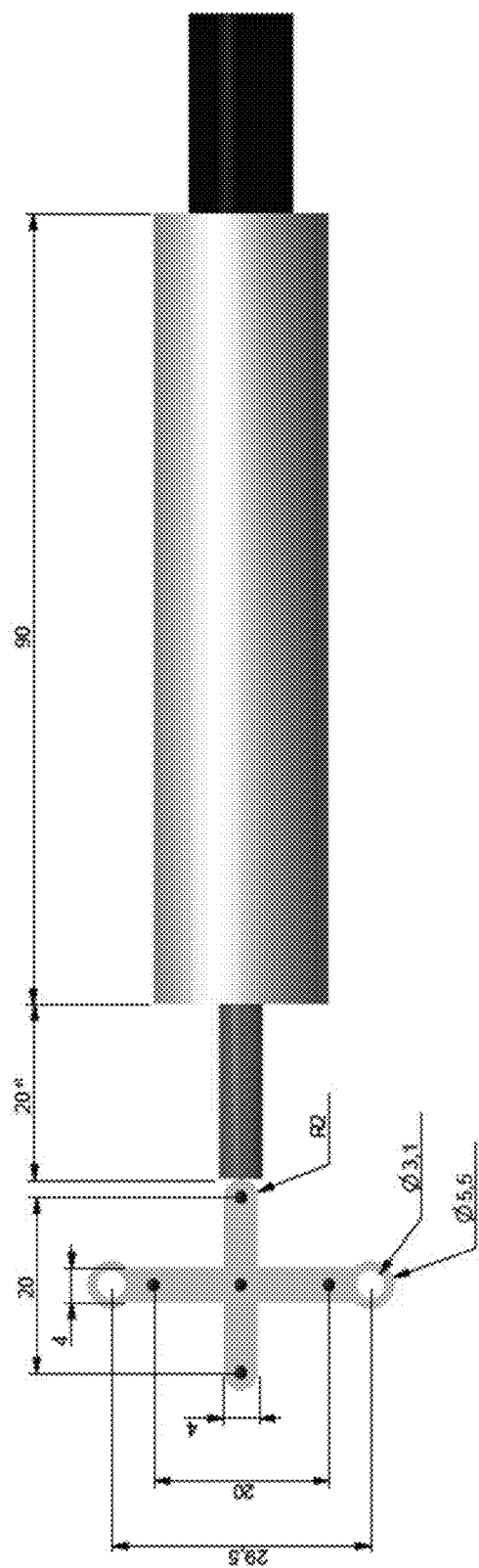
FIG. 20 is a bottom view parametric model drawing of an ionizing electrode assembly.
Figure 21C:
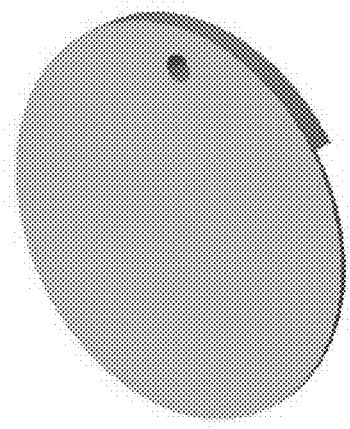
FIG. 21c is a perspective top view parametric model drawing of the ground electrode shown in FIGS. 21a and 21b.
Figure 21B:
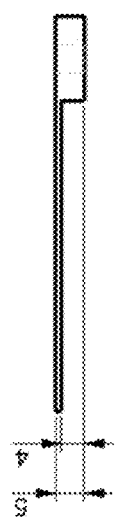
Figure 21A:
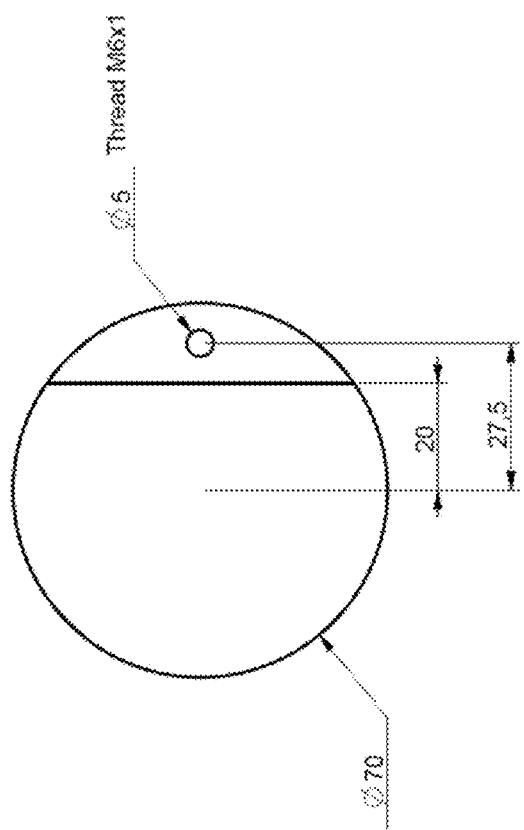
FIG. 21a is a bottom view of a ground electrode.

A fluid charging system is provided for charging fluids to be mixed with other fluids in a microfluidic system. The system includes a Fraser Model 7330 static generator connected to an ionizing electrode assembly via a high voltage cable. The ionizing electrode assembly includes a cross-shaped electrode comprising a cross-shaped stainless steel emitter plate and five (5) tungsten emitter pins. The ionizing electrode is connected to a 100 megaohm resistor unit via a high voltage lead. The ionizing electrode assembly has the dimensions and configuration shown in FIG. 20 (dimensions in millimeters). A ground electrode comprises a circular aluminum static ground plate that sits in a non-conductive acrylic holder. The ground electrode has the dimensions and configuration shown in FIGS. 21a, 21b, and 21c (dimensions in millimeters). The ground electrode is connected to the ground lug on the static generator.

Figure 22:
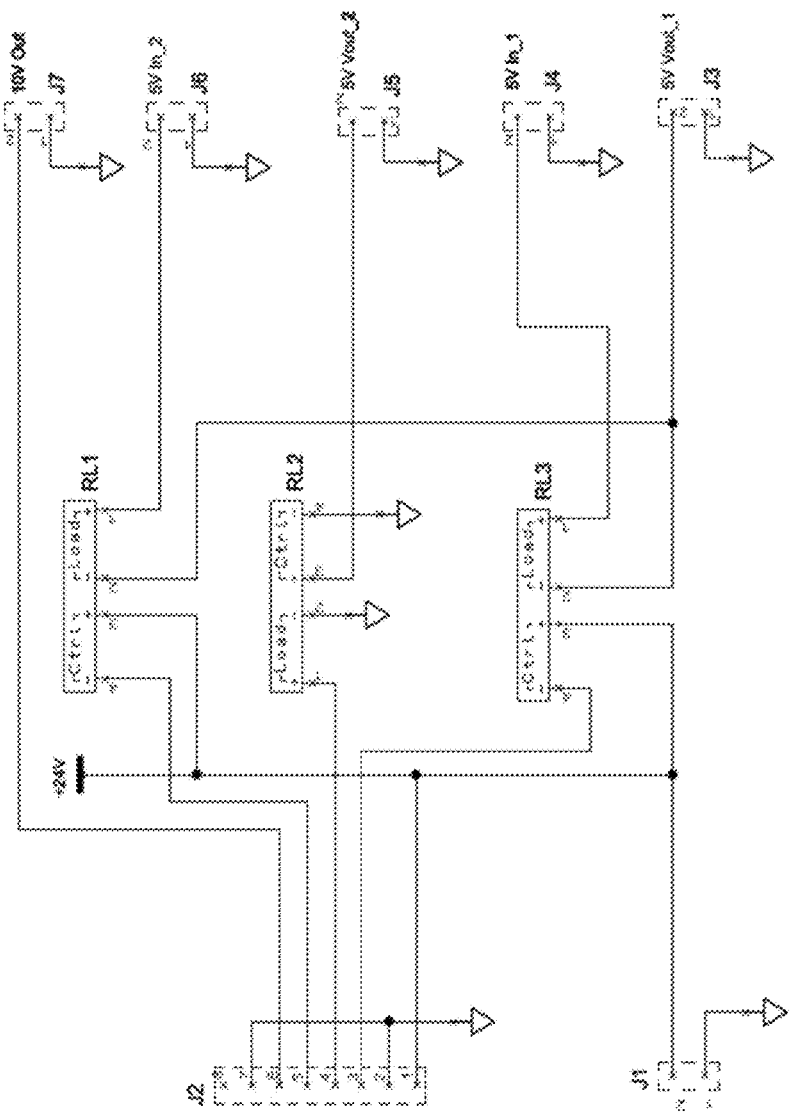
FIG. 22 is a circuit diagram for an interface between a static generator and a remote PC used to control a fluid charging system.
Figure 23:
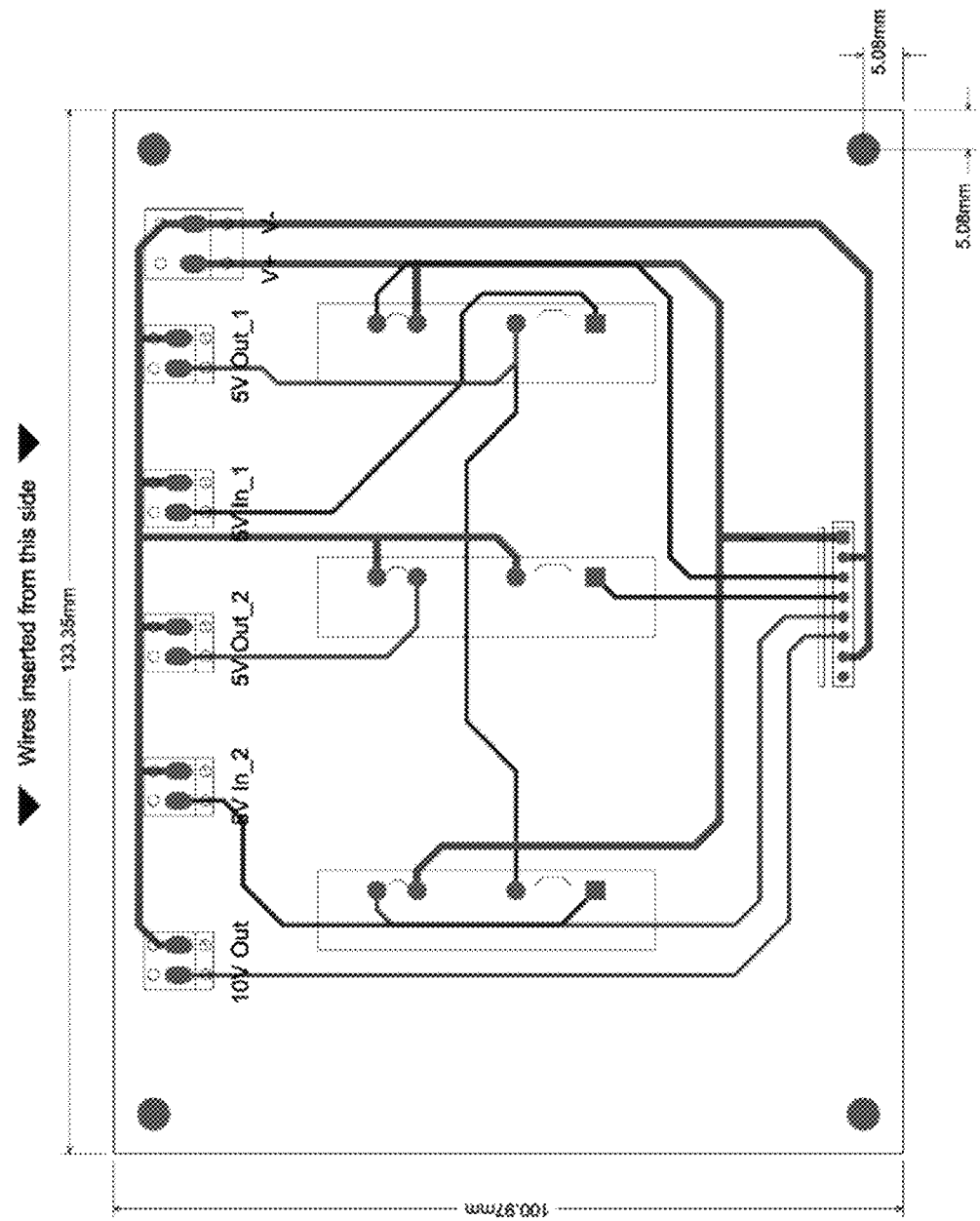
FIG. 23 is a circuit board layout diagram for an interface between a static generator and a remote PC used to control a fluid charging system.

The static generator uses solid state electronics and high frequency switching technology to provide stable electrical power output under a controlled current mode (up to 1.1 milliamps) or a controlled voltage mode (up to 20 kilovolts) from a 24 VDC supply. The static generator has a 0-10V analog controller input that is interfaced with a remote PC running a LabVIEW™ control program (National Instruments Corporation, http://www.ni.com/). The static generator and the remote PC are interfaced through a printed circuit board (PCB) having digital-to-analog conversion capability. FIGS. 22 and 23 show a circuit diagram and board layout, respectively, of the PCB interfacing the static generator and remote PC.

Figure 24:
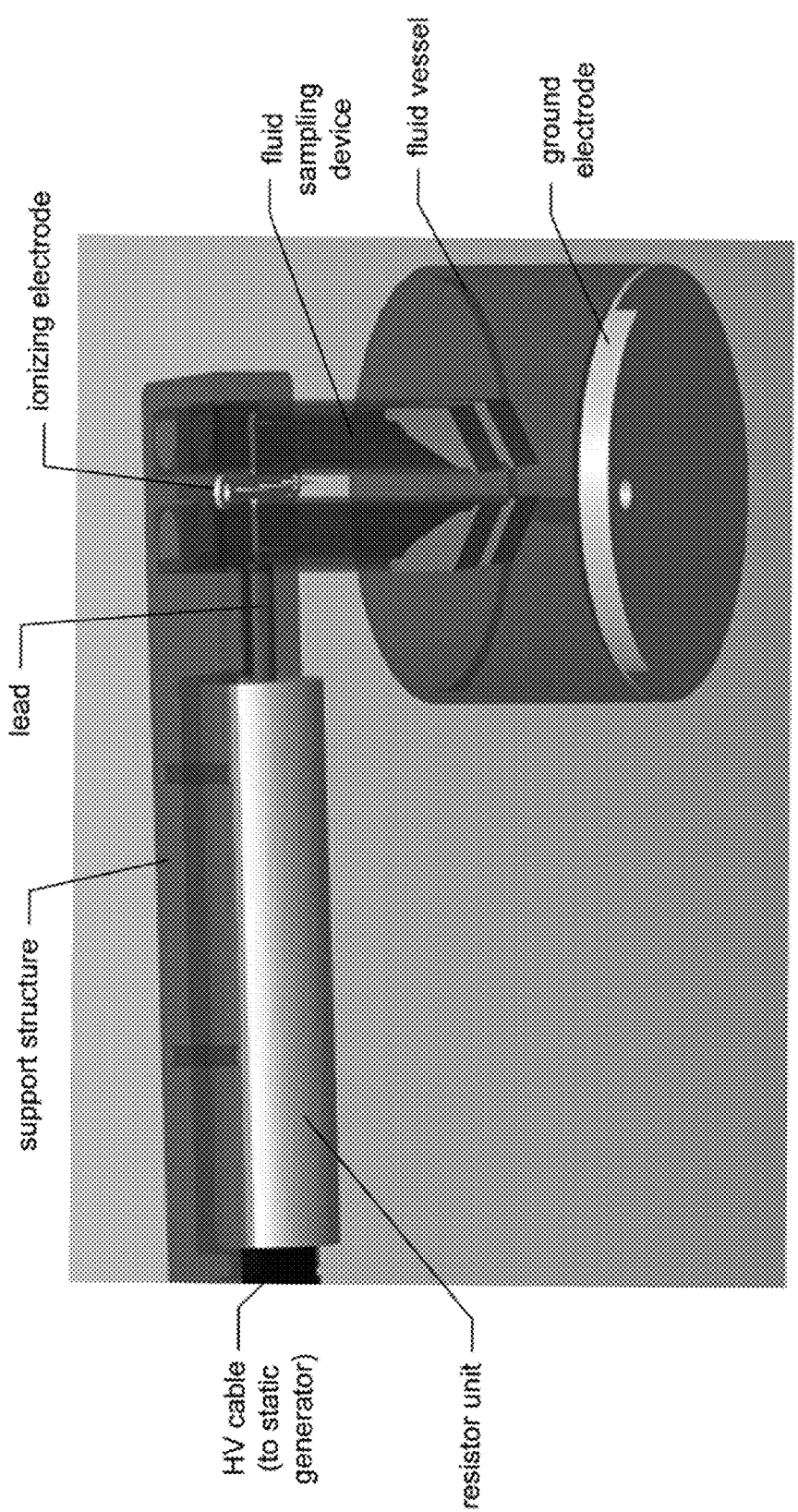
FIG. 24 is a perspective bottom view parametric model drawing of the electrode assembly shown in FIG. 20, the ground electrode shown in FIGS. 21a through 21c, a fluid vessel, and fluid sampling devices.

FIG. 24 shows the ionizing electrode and the ground electrode positioned adjacent to a glass fluid vessel. The ionizing electrode and the ground electrode are opposed so that the fluid vessel is positioned between the ionizing electrode and the ground electrode. The glass fluid vessel has an outer diameter that substantially matches the diameter of the ground electrode, the ground electrode and holder being dimensioned to seat and support the fluid vessel. Four (4) fluid sampling devices are positioned through open quadrant regions of the emitter plate of the ionizing electrode. The four (4) fluid sampling devices include sheaths surrounding tubes configured to withdraw fluid from the fluid vessel.

Example 2

The fluid charging system described in Example 1 is used to charge a first fluid. The fluid charging system described in Example 1 provides the first fluid with a net positive charge. The four (4) fluid sampling devices withdraw charged first fluid from the fluid vessel. The four (4) fluid sampling devices are in fluid communication with a microfluidic network including liquid bridges as described, for example, in United States Patent Application Publication Nos. 2008/0277494, 2010/0015606, 2010/0029512, 2010/0109320, and 2010/0297748, which are all incorporated by reference herein. The charged first fluid is mixed with one or more additional fluids in a liquid bridge. The charged first fluid and the one or more additional fluids are miscible. The net positive charge improves the mixing of the first fluid with the one or more additional fluids in the liquid bridge.

Example 3

The fluid charging system described in Example 1 is used to charge a first fluid comprising a master mixture. The fluid charging system described in Example 1 provides the first fluid with a net positive charge. The four (4) fluid sampling devices withdraw charged fluid comprising master mixture from the fluid vessel. The four (4) fluid sampling devices are in fluid communication with a microfluidic network including liquid bridges as described, for example, in United States Patent Application Publication Nos. 2008/0277494, 2010/0015606, 2010/0029512, 2010/0109320, and 2010/0297748, which are all incorporated by reference herein. The charged fluid comprising the master mixture is mixed with two additional fluids in a liquid bridge. The two additional fluids comprise DNA samples and reaction-specific reactants and are miscible with the charged fluid comprising the master mixture. The net positive charge improves the mixing of the first fluid with the two additional fluids in the liquid bridge.

The mixed fluid comprising the master mixture, DNA sample, and reaction-specific reactants is used to perform an amplification reaction. The liquid bridges are in fluid communication with a thermal cycler device configured to perform continuous-flow PCR, such as, for example, the devices described in United States Patent Application Publication Nos. 2008/0280331, 2010/009273, 2010/0092987, and 2010/0304446, which are all incorporated by reference herein. The mixed fluid comprising the master mixture, DNA sample, and reaction-specific reactants is microfluidically transported to the thermal cycler device where the PCR amplification reactions are performed.

Example 4

A negatively charged droplet may be formed as follows. An electrostatic pinner bar (SIMCO) is positioned above the master mix well creating a large electric field across the well. A voltage of 12-18 kV is typically applied across a distance of 50-80 mm. This has the effect of creating a differing charge density within the aqueous solution. Using a positive charge-generator produces a much higher concentration of negative ions at the top of the well. Since some enzymes, for example Taq enzymes, are neutrally charged, the enzyme remains unaffected by the charge separation. When a droplet is removed from the well, the fluid removed is from the upper negatively charged aqueous region resulting in a highly negatively charged droplet.

This specification has been written with reference to various non-limiting and non-exhaustive embodiments. However, it will be recognized by persons having ordinary skill in the art that various substitutions, modifications, or combinations of any of the disclosed embodiments (or portions thereof) may be made within the scope of this disclosure. Thus, it is contemplated and understood that the present disclosure embraces additional embodiments not expressly set forth herein. Such embodiments may be obtained, for example, by combining, modifying, or reorganizing any of the disclosed steps, components, elements, features, aspects, characteristics, limitations, and the like, of the various embodiments described herein. In this manner, Applicants reserve the right to amend the claims during prosecution to add features as variously described herein in compliance with the requirements of 35 U.S.C. §112, first paragraph, and 35 U.S.C. §132(a).

What is claimed is:
1. A fluid charging system comprising:
an ionizing electrode positioned adjacent to a fluid vessel;
a ground electrode positioned adjacent to the fluid vessel, the fluid vessel positioned between the ionizing electrode and the ground electrode;
wherein the ionizing electrode and the ground electrode are configured to produce an ion field that charges fluid contained in the fluid vessel;
a fluid sampling device configured to withdraw fluid from the fluid vessel; and
a liquid bridge in fluid communication with the fluid sampling device, wherein the liquid bridge comprises: (i) a first inlet port in fluid communication with the fluid sampling device, and (ii) a second inlet port in fluid communication with a source of immiscible carrier fluid;
wherein the liquid bridge is configured to form liquid droplets, and wherein the liquid droplets contain the fluid from the fluid vessel and are enveloped within the immiscible carrier fluid.

2. The fluid charging system of claim 1, further comprising an electrical power source connected to the ionizing electrode.

3. The fluid charging system of claim 2, wherein the electrical power source comprises a static generator.

4. The fluid charging system of claim 1, further comprising a resistor unit connected to the ionizing electrode.

5. The fluid charging system of claim 1, further comprising:

an electrical power source connected to the ionizing electrode; and a resistor unit connected in series between the electrical power source and the ionizing electrode.

6. The fluid charging system of claim 1, further comprising:
   a static generator connected to the ionizing electrode; and
   a resistor unit connected in series between the static generator and the ionizing electrode.

7. The fluid charging system of claim 1, wherein the ionizing electrode comprises:
   an emitter plate; and
   a plurality of emitter pins connected to the emitter plate.

8. The fluid charging system of claim 1, wherein the ionizing electrode comprises:
   a stainless steel emitter plate; and
   a plurality of emitter pins connected to the emitter plate, the emitter pins comprising tungsten.

9. The fluid charging system of claim 1, wherein the ionizing electrode comprises:
   a stainless steel emitter plate; and
   a plurality of tungsten carbide or tungsten alloy emitter pins connected to the emitter plate.

10. The fluid charging system of claim 1, wherein the ground electrode comprises an aluminum or aluminum alloy ground plate.

11. The fluid charging system of claim 1, wherein the ionizing electrode comprises:
    an emitter plate having a cross-shape comprising a first member and an intersecting second member; and
    at least five emitter pins connected to the emitter plate at opposed ends of the first member, at opposed ends of the second member, and at an intersection of the first member and the second member.

12. The fluid charging system of claim 1, further comprising a fluid sampling device configured to withdraw fluid from the fluid vessel, the fluid sampling device comprising a plurality of tubes in fluid communication with the fluid vessel.

13. The fluid charging system of claim 12, wherein the ionizing electrode comprises:
    an emitter plate having a cross-shape comprising a first member and an intersecting second member; and
    a plurality of emitter pins connected to the emitter plate;
    wherein at least one tube is positioned through an open quadrant region of the emitter plate.

14. The fluid charging system of claim 1, further comprising a fluid sampling device configured to withdraw fluid from the fluid vessel, the fluid sampling device comprising a plurality of sheaths, wherein each sheath surrounds a plurality of tubes.

15. The fluid charging system of claim 14, wherein the ionizing electrode comprises:
    an emitter plate having a cross-shape comprising a first member and an intersecting second member; and
    a plurality of emitter pins connected to the emitter plate;
    wherein at least one sheath is positioned through an open quadrant region of the emitter plate.

16. The fluid charging system of claim 1, wherein the liquid bridge is configured to form the liquid droplets by adjustment of flow rate for the fluid or the immiscible carrier fluid.

17. The fluid charging system of claim 1, wherein the liquid bridge is configured to form the liquid droplets by joining one or more liquid droplets to a first liquid droplet.

18. The fluid charging system of claim 1, wherein the liquid bridge is further configured to merge the liquid droplets with other liquid droplets.

19. The fluid charging system of claim 18, wherein the other liquid droplets include a master mixture fluid or a biological sample.

20. The fluid charging system of claim 19, wherein the other liquid droplets include a biological sample, and wherein the biological sample comprises DNA.

21. The fluid charging system of claim 18, wherein the other liquid droplets are uncharged.

22. The fluid charging system of claim 18, wherein the other liquid droplets are charged.

23. The fluid charging system of claim 18, wherein the liquid bridge further comprises a third inlet port, and wherein the liquid bridge is configured to form the other liquid droplets at the third inlet port.

24. The fluid charging system of claim 20, further comprising:
    a thermal cycler.

25. The fluid charging system of claim 24, further comprising:
    an optical detection device connected to the thermal cycler.

* * * * *